(12) United States Patent
LaBelle et al.

(10) Patent No.: US 7,067,293 B2
(45) Date of Patent: Jun. 27, 2006

(54) NANOENGINEERED BIOPHOTONIC HYBRID DEVICE

(76) Inventors: Jeffrey T. LaBelle, 1859 E. Flores Dr., Tempe, AZ (US) 85282; Vincent B. Pizziconi, 3435 E. Highline Canal Rd., Phoenix, AZ (US) 85042

(*) Notice: Subject to any disclaimer, the term of this patent is extended or adjusted under 35 U.S.C. 154(b) by 0 days.

(21) Appl. No.: 10/658,541

(22) Filed: Sep. 8, 2003

(65) Prior Publication Data

US 2006/0008893 A1    Jan. 12, 2006

Related U.S. Application Data

(60) Provisional application No. 60/408,775, filed on Sep. 7, 2002.

(51) Int. Cl.
  *C12N 13/00*   (2006.01)
  *C12N 11/14*   (2006.01)
  *C12N 1/20*    (2006.01)
  *C12M 1/36*    (2006.01)
  *C12M 1/00*    (2006.01)

(52) U.S. Cl. ............... 435/173.4; 435/176; 435/286.1; 435/283.1; 435/252.1

(58) Field of Classification Search ............ 435/173.4, 435/176, 286.1, 283.1, 243, 252.1
See application file for complete search history.

(56) References Cited

U.S. PATENT DOCUMENTS

| | | |
|---|---|---|
| 3,935,031 A | 1/1976 | Adler |
| 4,103,064 A | 7/1978 | McAlear et al. |
| 4,149,902 A | 4/1979 | Mauer et al. |
| 4,190,950 A | 3/1980 | Skotheim |
| 5,466,301 A | 11/1995 | Hammerbacker et al. |
| 5,504,573 A | 4/1996 | Cheiky-Zelina |
| 5,573,909 A | 11/1996 | Singer et al. |
| 5,711,915 A | 1/1998 | Siegmund et al. |
| 5,976,892 A | 11/1999 | Bisconte |
| 6,079,415 A | 6/2000 | Bernerd et al. |
| 6,342,389 B1 | 1/2002 | Cubicciotti |
| 6,476,312 B1 | 11/2002 | Barnham |
| 6,538,191 B1 | 3/2003 | MacDonald |
| 6,603,069 B1 | 8/2003 | Muhs et al. |

OTHER PUBLICATIONS

He et al., Bacteriorhodopsin thin film assemblies- immobilization, properties and applications, Advanced Materials 11(6):435-446, 1999.*

Miyasaka et al., "Quantum conversion and image detection by a bacteriorhodopsin-based artificial photoreceptor," Science 255(5042):342-344, 1992.*

(Continued)

*Primary Examiner*—Robert A. Wax
*Assistant Examiner*—Rosanne Kosson
(74) *Attorney, Agent, or Firm*—Gallagher & Kennedy, P.A.; Thomas D. MacBlain

(57) ABSTRACT

An improved method for the design and development of high performance hybrid devices having biological and nonbiological components. A figure of merit is developed for the biological component or components. The component is subjected to various environmental variables as it or its biological source organism is grown. The biological component is force adapted to cause its figure of merit to reach a goal or an acceptable measure. The biological component is used in hybrid constructs that may be nanostructures, given the small size of the biological parts. In one specific embodiment, force-adapted chlorosomes of *C. aurantiacus* enhance performance of a silicon photovoltaic cell. The bacteria, *Chloroflexus aurantiacus* (*C. aurantiacus*), strain J-10-fl, has the A.T.C.C. designation number 29366, having been deposited in July, 1976.

9 Claims, 15 Drawing Sheets

OTHER PUBLICATIONS

Planner et al., "The influence of rigid matrices on the processes of deactivation of excited bacteriochlorophyll c," Journal of Photochemistry and Photobiology A: Chemistry 115:151-155, 1998.*

LaBelle, Design feasibility of a nanoscale biophotonic hybrid device, Ph.D. Disseration, Arizona State University, Dec. 2001.*

Pizziconi et al., Preview before Submission, NSF Project Report, Version 1.2, printed from the Internet on Sep. 6, 2002.*

LaBelle et al., "Nanoengineered interface for biophotonic hybrid device components," MCTB Lab, Dept. of Bioengineering, Arizona State University, undated publication.*

LaBelle et al., "Nanoscale biophotonic hybrid biosensor," MCTB Lab, Dept. of Bioengineering, Arizona State University, undated publication.*

Terpugov et al., "FTIR emission spectra of bacteriorhodopsin in a vibrational excited state," Biochemistry (Moscow) 66(11):1315-1322, 2001.*

Anderson, B.B. et al. "Grating Light Reflection Spectroscopy for Determination of Bulk Refractive Index and Absorbance" Anal. Chem. 1996, 68, 1081-1088.

Borrego, C.M. et al. "Light intensity effects on pigment composition and organisation in.. " Photosynthesis Research 59; 159-166, 1999, Kluwer Academic Publishers, Netherlands.

Bunce, J.A. "Acclimatin to temperature of the response of photosynthesis to increased . . . " Photosynthesis Research 64; 89-94, 2000, Kluwer Academic Publishers, Netherlands.

Cedeno, C.C. et al. "Nanoimprint lithography for organic electronics" Microelectronic Engineering 61-62, 2002 25-31.

Dragoman, D. et al., "Optical modelling of quantum dots" Optics Communications 150, 1998, 331-338.

Fendler, J.H. "Self-assembled nanostructured materials" Chem. Mater. 1996, 8, 1616-1624.

Foidl, M. et al. "PHototrophic growth and chlorosome formation in Chloroflexus . . . " Photosynthesis Research 54, 219-226, 1997, Kluwer Academic Publishers, Netherlands.

Gilardi, G. et al. "Manipulating redox systems: applicatin to nanotechnology" TRENDS in Biotechnology vol. 19 No. 11, Nov. 2001.

Green, M.A., "Prospects for photovoltaic efficiency enhancement using low-dimensional structures" Nanotechnology 11, 2000, 401-405, printed in the UK.

Hall, D.J. "An experimental approach to the dynamics of a natural population of Daphnia Galeata Mendotae" Ecology, vol. 45, 1, Jan. 1964, 94-112.

He, J. et al. "Structure and optical properties of self-assembled InAs/GaAs quantum dots with . . . " Journal of Crystal Growth 240, 2002, 395-400.

He, Jin-An et al. "Bacteriorhodopsin thin film assemblies—immobilization, properties and applications" Adv. Mater. 1999, 11, No. 6, 435-446.

Inoue, N. et al. "Effects of high-temperature treatments on a thermophilic Cyanobacterium *Synechococcus vulcanus*" Plant Cell Physiol. 41(4); 515-522 (2000).

Koti, A.S.R. et al. "Self-Assembly of Template-Directed J-Aggregates of Porphyrin" Chemistry of Materials vol. 15 No. 2, Jan. 28, 2003.

Muramatsu, K. et al. "Two-Diemsnional Assemblies of Colloidal SiO2 and TiO2 Particles Prepared by the . . . " Journal of Colloid and Interface Science 242, 127-132 (2001).

Maruyama, T. et al. "Energy conversion efficiency of solar cells coated with fluorescent coloring agent" Solar Energy Materials & Solar Cells 56 (1998) 1-6.

Maruyama, T. et al. "Wedge-shaped light concentrator using total internal reflection" Solar Energy Materials & Solar Cells 57 (1999) 75-83.

Narayan, K.S. et al. "Dual function hybrid polymer-nanoparticle devices" Applied Physics Letters vol. 74 No. 6, Feb. 8, 1999.

Olive, J. et al. "Ultrastructure and light adaptation of phycobilisome mutants of Synechocystis PCC 6803" Biochimica et Biophysica Acta 1319 (1997) 275-282.

Peled, A. et al. "Photobleaching and photodeposition in a chlorophyll based solution" Synthetic Metals 115 (2000) 167-171.

Planner, A. et al. "The influence of rigid matrices on the processes of deactivation of excited . . . " Jurnal of PHotochemistry and Photobiology A: Chemistry 115 (1998) 151-155.

Rasmussen, K.O. et al. "Nonlinear and stochastic modelling of energy transfer in Scheibe aggregates" Mathematics and Computers in simulation 40 (1996) 339-358.

Sanchez-Cortes, S. et al. "Influence of coverage in the surface-enchanced Raman scattering of cytosine and its methyl derivatives on . . . " Surface Science 473 (2001) 133-142.

Sawicki, D.A. et al. "Universal relationship between optical emission and absorption of complex systems: an alternative approach" Physical Review A, vol. 54 No. 6, Dec. 19.

Schmidt, K.A. et al. Combined fluorescence and photovoltage studies on . . . Photosynthesis Research 58; 43-55, 1998, Kluwer Academic Publishers, Printed in the Netherlands.

Sommeling, P.M. et al. "Spectral response and IV-characterizatin of dye-sensitized nanocrystalline TiO2 solar cells" Solar Energy Materials & Solar Cells 62 (2000) 399-410.

Stangl, R. et al. "On the Modeling of the dye-sensitized solar cell" Solar Energy Materials and Solar Cells 54 (1998) 255-265.

Umetsu, M. et al. "How the formation process influences the structure of . . . " Photosynthesis Research 60; 229-239, 1999 Kluwer Academic PUblishers, printed in the Netherlands.

Wagner, J. et al. "Characterization of Monodisperse Colloidal Particles: Comparison between SAXS and DLS" langmuir 2000, 16, 4080-4085.

Weetall, H.H. et al. "Optical and electrical characteristics of bacteriorhodopsin gelatin films and tin-oxide coated electrodes" Current Applied Physics 3 (2003) 281-291.

Yang, T. et al. "Creating Addressable Aqueous Microcompartments above Solid Supported Phospholipid Bilayers Using Lithographically . . . " Anal. Chem. 2000, 72, 2587-2589.

Tamiaki, H. et al "Aggregation of synthetic metallochlorins in hexane. A model of chlorosomal bacteriochlorophyll self-assemblies . . . " photosynthesis Research 59-67, 2002.

Arellano, Juan B. et al, "Effect of Carotenoid Biosynthesis inhibition on the chlorosome organization . . . ," Photochemistry and Photobiology, 2000, 71 (6): 715-723.

Gerola, Paolo D. et al, "A new bacteriochlorophyll a-protein complex associated with chlorosomes of green sulfur bacteri . . . ," Biochimica et Biophysica Acta 848 (1986), 69-76.

Zhu, Y. et al., "Microscopic and spectroscopic studies of untreated and hexanol-treated chlorosomes from Chloroflexus . . . ," Biochimica et biophysica Acta 1232 (1995) 197-207.

* cited by examiner

3 μm

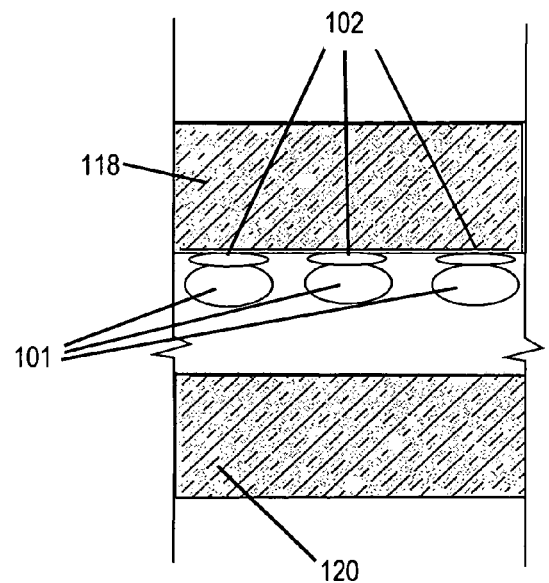
Fig. 12
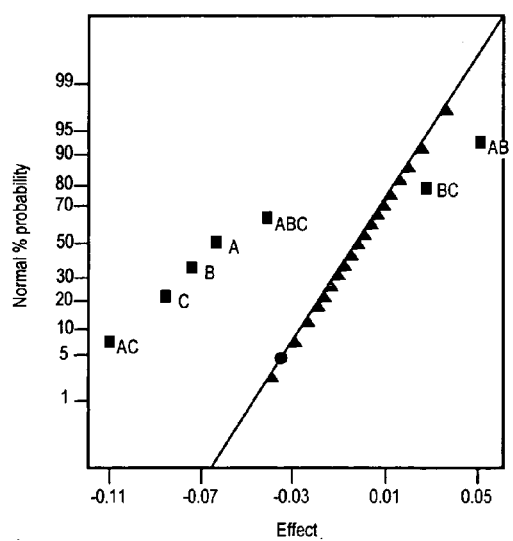 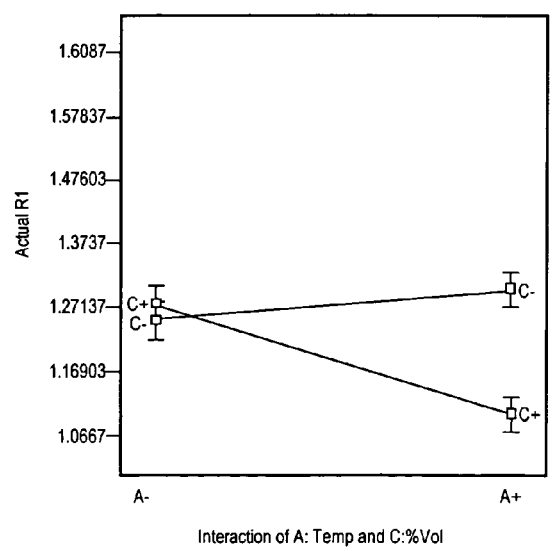
Fig. 13a          Fig. 13b

$$\text{Photonic Figure of Merit} = \frac{\%T_{440} \text{ (Bchl c Soret)}}{\%T_{440} \text{ (Bchl c Soret)} + \%T_{460} \text{ (carotenoid)}} \times \frac{\%T_{795} \text{ (Bchl a Baseplate)}}{\%T_{740} \text{ (Bchl c oligomeric } Q_y)}$$

|  | %T 795 | %T 740 | %T 460 | %T 440 |
|---|---|---|---|---|
|  | Bchl a | Bchl c | carotenoid | Soret |
| Well 1 | 0.9625 | 0.6067 | 0.6417 | 0.7034 |
| Well 21 | 0.9555 | 0.8044 | 0.5703 | 0.5985 |
| Well 22 | 0.9502 | 0.7948 | 0.565 | 0.5908 |
| Well 23 | 0.9553 | 0.8997 | 0.8599 | 0.8671 |
| Well 24 | 0.9569 | 0.9237 | 0.8731 | 0.8736 |
| Well 26 | 0.9566 | 0.8732 | 0.7793 | 0.7895 |
| Well 28 | 0.9541 | 0.6126 | 0.6421 | 0.7161 |

NANOENGINEERED BIOPHOTONIC HYBRID DEVICE

CROSS REFERENCE TO RELATED APPLICATIONS

This application claims priority from the provisional patent application Ser. No. 60/408,775 filed Sep. 7, 2002 in the name of Jeffrey T. LaBelle and Vincent B. Pizziconi entitled "Method & Apparatus for Synthesis, Processing, Design & Manufacturing of High Performance, Scalable & Adaptive, Robust Energy-Interactive Materials, Devices & Systems" incorporated herein by reference.

STATEMENT OF GOVERNMENT FUNDING

Financial assistance for this project was provided by the U.S. Government through the National Science Foundation Under Grant Numbers 9602258 and 9986614 and the United States Government may own certain rights to this invention.

FIELD OF THE INVENTION

This invention relates to hybrid biological and electronic photosensitive devices and more particularly to nanoscale hybrid devices of this kind and their method of manufacture.

BACKGROUND

Recently, attempts to marry biology and engineering to create various biohybrid constructs have been steadily increasing. A limited number of novel biohybrid sensor applications have already been reported, and in some cases commercialized, that incorporate "smart" molecular-scale biological components. These have attracted considerable interest from both the biomedical and biotechnology communities worldwide. However, little has been done to date in developing integrated nanodevices and systems such as microanalytical systems incorporating novel, engineered nanobioconstructs and their analogues for use in integrated nanodevices and systems such as bio-optical hybrid sensors capable of very sensitive and selective nanoscale detection due to enhanced performance characteristics as determined by a prescribed biohybrid Figure of Merit (FoM). Potential applications include microsystem applications requiring low-level light detection capability (e.g. micro total analytical systems (µTAS) for immunoassay, genomics and proteomics), such as "point-of-care" diagnostic medicine, biotechnology, space bioengineering, and countermeasures to biowarfare for defense.

In general, the current state of art for engineering design as taught by Koen (Koen, 1987) and many others (Otto and Wood, 2001), has not led to the achievement of device components, stand-alone devices, nor engineered systems that function or otherwise perform at a prescribed FoM and oftentimes typically perform at levels significantly below optimal FoM levels and theoretically achievable maximum FoM limits.

The well known area of thermoelectric device design exemplifies the present ability of engineering design heuristics to achieve a desirable thermoelectric FoM (i.e., ZT) that significantly exceeds current ZT device values of ~1 although a ZT value of 4 is theoretically possible (Rowe, D. M., 1995). The present inability by those skilled in the art to achieve desired material and device FoM's is essentially true for virtually all engineering device design applications spanning diverse disciplinary fields and broad industry product segments.

In recent years, less effective and predictive empirical approaches have been used to devise novel hybrid devices that incorporate naturally-derived, or mimetics thereof, biological materials and constructs that have resulted in enhanced device performance relative to their non-hybrid engineered counterpart. To date, however, the engineering method does not teach how to design, select, modify or otherwise alter smart, nanoscale energy-interactive materials (e.g., molecular-scale biophotonic components) derived from natural or biomimetic analog constructs, a priori, in spite of their intrinsically superior and potentially adaptable structural and performance characteristics. Nor does the engineering method show those skilled in this art how such nanoscale materials can be further embodied or employed as components, or as stand-alone devices, that are capable of producing robust and scalable energy-interactive biohybrid devices and systems, a priori, to function at a desired FoM not yet achievable by conventional engineering means.

Photoactive semiconductors such as Si photovoltaic cells (as one example of a large scale device) have long been known. They have been employed in various devices and applications for years. Their varying responsivity to certain light wavelengths throughout the visible spectrum has been observed as well. On the biological side, thermophilic photosynthetic bacteria such as *Chloroflexus aurantiacus* (*C. aurantiacus*) and other species have been studied and reported upon. The photosensitive "antenna" cells, "chlorosomes," of these organisms have been studied and reported upon, as well. Perhaps as a result of inconsistency of results with photosynthetic bacteria, these organisms and their chlorosomes have not been incorporated into useable devices. There has been no successful synthesis of photosensitive semiconductor materials with the chlorosomes of photosynthetic bacteria reported. A need exists for improvement of the performance of photoactive devices throughout the light spectrum, and for techniques for using the good photosensitivity of photosynthetic bacteria in photoactive devices. More fundamentally, there is a need to identify inconsistencies in the photosensitivity (or other photonic or electroactivity) of biological specimens and to apply a method or methods to ameliorate or eliminate such inconsistencies.

As one means of gathering knowledge about a system, Design of Experiment (DOE) analysis is a widely used statistical modeling approach, reported in detail elsewhere (Montgomery, 1991). A unique advantage of DOE, particularly as applied to complex adaptive systems, is its ability to elucidate, not only the effect of the controlling variables, but also their complex interactions. Use of DOE analysis with biological or hybrid biological/nonbiological devices and systems has not been encountered. In particular use of the powerful DOE approach in connection with forced adaptation in biological systems (such as bacteria) to move the systems toward a more consistent (i.e. dependable) performance is not known. Figure of Merit (FoM) is another concept often used in engineering (among other fields such as economics, chemistry, astronomy, etc.). FoM is a measure of a device's performance. It is used in many contexts. However FoM as a design-driving measure, particularly with respect to adaptive biological organisms-based systems, devices and components is considered to be a radical departure from other uses of this concept. Further, as applied to biological organisms, parts thereof or systems made up of such organisms, a means to control multiple environmental variables is needed if the DOE approach is to be applied.

The transfer function of a device, circuit or system is another engineering concept that is well understood. However, that concept has not ordinarily been applied to biological systems, if at all. A need exists to apply engineering concepts like DOE, FoM and the transfer function to the analysis, evaluation and design of biological, bioengineered and hybrid systems, components and devices.

SUMMARY

Broadly, the present invention encompasses equipment and methods for the synthesis, processing, design and manufacturing of high performance, scalable, adaptive and robust energy-interactive hybrid materials, devices and systems combining biological and nonbiological technologies. Specifically, an exemplary embodiment of the invention adapts powerful engineering concepts to the engineering of biological components that are to be used in manufactured devices and systems, including hybrid devices and systems.

FIG. 1 exemplifies a novel method that will guide those skilled in the art to achieve the design and development of high performance hybrid materials and devices. As illustrated, several key steps are depicted in FIG. 1 that show one skilled in the art how to achieve desired and even optimal hybrid device designs that utilize smart, nanoscale constructs acquired, harvested or otherwise derived directly from complex living organisms. A preferred embodiment is the use of a multiple input-multiple output apparatus, such as a multiple input-multiple output environmental chamber (i.e., MIMO/EC), and applicable computational algorithms to extract useful and exploitable hybrid device design heuristics. Use of this method will result in a desired and prescribed Figure of Merit in spite of the use of previously unknown or poorly defined or characterized nanoscale biological constructs and their function. In applied form, the novel engineering design method described herein will provide a means to identify or otherwise exploit intractable, or very difficult to identify, useful engineering specifications. A preferred embodiment of this invention is shown in FIG. 2, an illustration of a novel method and apparatus for the design and development of high performance hybrid materials and devices.

One application of the proposed invention is the enhancement of well-known photoactive semiconductor devices, such as Si photovoltaic cells using nanoscale biophotonic constructs that are either acquired, harvested or otherwise manipulated in their natural or adapted state using the method and apparati described herein to achieve desired FoM performance characteristics. Although commercially available Si photovoltaic cells have been employed in various devices and applications for years, their FoMs are typically low despite detailed knowledge of their structure and function and the ability to prescribe device performance specifications from use of selected light wavelengths throughout the visible spectrum, as well as, related device specifications associated with the engineering transfer function.

The transfer function of a component, device, or system is a useful engineering concept, directly related to the FoM, that is well known and understood by those skilled in the art. However, the use of a transfer function and related FoM concepts have not been generally applied and prescribed to biological constructs intended for use in the design of biohybrid devices and systems, if at all. Thus, an unmet and nonobvious need still exists to use well known engineering heuristics such as, the design of experiments (i.e., DOE), FoM and the transfer function for the analysis, design, and evaluation of bioengineered hybrid components, devices and systems.

To demonstrate the novelty and utility in the use of the hybrid device design heuristic to achieve high performance hybrid materials and devices (FIG. 2), the invention described herein improves the device performance (i.e., the FoM) of a stand-alone, commercial silicon photovoltaic device (Si PV) using a nanoscale bioderived construct with generally unknown engineering specifications. However, the methods and apparati taught herein generally apply to the design and exploitation any smart nanoscale or integrative nanoscale material, construct, or system, or mimics thereof, that is amenable to the FoM enhancement of a hybrid device or system.

A typical FoM of a Si PV device is generally less than 1 and typically only ~0.28–0.32. Although a number of potentially useful hybrid design approaches can be employed to improve the SiPV FoM using the invention taught herein, the use of a nanoscale biophotonic construct having desired complementary energy transfer properties constitutes a potentially viable hybrid design approach. One such nanoscale biophotonic construct having potentially useful and exploitable engineering specifications to enhance the FoM of a photonic device, such as a SiPV device, is the nanoscale pigment-protein supramolecular construct known as a light antenna structure that function as energy funnels in thermophilic photosynthetic bacteria such as *Chloroflexus aurantiacus* (*C. aurantiacus*) and other photosynthetic species. These highly quantum efficient photosensitive constructs (also known as "chlorosomes") are known to perform significant photonic energy shifts (red shift). In the case of the chlorosome associated with the *C. aurantiacus*, an input photonic energy at a wavelength of ~460–480 nm is typically shifted to ~800–820 nm with very little energy loss.

Typically SiPV devices are more sensitive to higher photonic wavelengths and generally most sensitive to the near infrared region (i.e. 800–900 nm) of the electromagnetic spectra. Thus, in principle, the use of biologically-derived light antenna structures, as well as mimics or analogs thereof, could potentially enhance the FoM of a Si PV device if exploitable engineering specification(s), such as the transfer function or its associated FoM, could be identified, acquired, developed and subsequently employed successfully in a SiPV engineered hybrid device or system that meets a prescribed and verifiable FoM that validates the desired performance of the hybrid biophotonic device. However, the achievement of desired FoMs using hybrid device and system approaches is not obvious to those skilled in the art of device design and development and empirical combinations of smart materials or components used in the design and manufacture hybrid device can oftentimes lead to device and system performances (i.e., FoM) inferior to nonhybrid device and system counterparts.

A preferred embodiment of the invention makes use of well-known design algorithms, such as the Design of Experiment (DOE), among many others known and appreciated by those skilled in the art. DOE analysis is a widely used statistical modeling design tool reported in detail elsewhere (Montgomery, 1991). A unique advantage of DOE, particularly as applied to complex adaptive systems, is its ability to elucidate, not only the effect of the controlling or independent variables, but also their oftentimes complex interactions.

The use of DOE analysis in combination with a novel MIMO/EC apparatus can be used to identify, acquire or otherwise produce useful and exploitable engineering hybrid device and system specifications from complex biological constructs in their isolated or natural state or environment, or mimics thereof. In particular, the combined use of DOE with the MIMO/EC apparatus can provide a novel and powerful design heuristic to achieve desired engineering specifications of nanoscale-based constructs via their identification and/or modification from complex, adaptive systems, such as, viable organisms.

The use of the DOE-MIMO/EC apparatus in this embodiment is most useful when it may be desirable to modify one or more properties of a complex, adaptive construct through the 'forced adaptation' of a modifiable biological component of a viable, complex systems (such as bacteria). This produces the desired modification of a potentially useful property or characteristic of e.g. a nanoscale-based component that is useful to achieve a desired performance level (i.e. FoM) of a device or system in which that is not otherwise achievable by its nonhybrid.

In one embodiment of the invention by varying the environmental conditions under which a biological component of, for example, a hybrid device, is grown, a transfer function for that component can be altered. Using the MIMO/EC of this invention, a biological component may be force adapted in such a manner as to affect a modification of a transfer function that governs its outputs under given inputs. The desired transfer function can thus be engineered into a biological component, within bounds.

In one exemplary embodiment of the invention, the methods and equipment of the invention are used to engineer an exemplary hybrid photoactive component. That component combines a hitherto acceptable photoactive semiconductor device with a biological mechanism that has extreme high photoactive performance to achieve performance unprecedented in devices of the type. This hybrid device, itself an exemplary and preferred embodiment of one aspect of this invention, uses a constituent of a photosynthetic bacterium to enhance the response of a semiconductor photoactive device across the intended spectrum of its use.

With the methods and equipment of this invention, chlorosomes of the thermophilic green photosynthetic bacterium *Chloroflexus aurantiacus* (*C. aurantiacus*) are successfully coupled to a photoactive semiconductor device to derive enhanced performance across the relevant spectrum.

Here, using design of experiment (DOE) methodology, adaptive biological units, such as cells, are force-adapted to achieve consistent performance in the characteristics of interest. In this, a multiple input-multiple output environment chamber (the above-mentioned MIMO/EC) affords the ability to force adapt the bacteria from which these chlorosomess are gathered.

This embodiment is focused on exploiting biosystems at the nanoscale for their utility as functional 'device' components in a proposed biohybrid microdevice. More specifically, a design feasibility study was implemented to evaluate the efficacy of a naturally occurring nanoscale biophotonic, light adaptive 'antenna' structure (the chlorosome), isolated from *C. aurantiacus*. The overall objective was to assess its utility as functional device component that would enhance the spectral performance characteristics of well-characterized photonic devices, i.e., solid-state photovoltaic.

The chlorosomes are nanoscale, optical functional units (100×30×10 nm). They can transfer photonic energy at high quantum efficiencies (69–92%) and ultra-fast rates (picoseconds), were fabricated into programmed arrays on solid substrates and fully characterized. These biological assemblies were subsequently integrated with the well-characterized photodetectors and evaluated for their potential to selectively enhance performance the spectral regions where the photodetectors are inherently insensitive.

BRIEF DESCRIPTION OF THE DRAWINGS

FIG. 12 is an enlarged fragmentary cross-sectional view along the line 12—12 of FIG. 11 and shows the chlorosomes like that of FIG. 6 adherent to a transparent plate;

FIG. 13a is a normal percentage probability plot and FIG. 13b is the interaction plot between temperature and percent volume for a design of experiments analysis where the output variable to be studied was the ratio R1 of absorbance at 740 nm to absorbance at 808 nm;

DETAILED DESCRIPTION

The bacteria, *Chloroflexus aurantiacus* (*C. aurantiacus*), strain J-10-fl, has the American Type Culture Collection (ATCC) designation number 29366, having been deposited in July, 1976. The ATCC is located at 10801 University Boulevard, Manassas, Va. 20110-2209 U.S.A. The *C. aurantiacus* bacteria is a green, nonsulfur, flexing/gliding, photosynthetic bacteria. It is thermophilic and can be found in hot springs up to temperatures of 70° C. in large mat-like layers. The layers, when concentrated enough, have an orange coloration.

Figure 3:
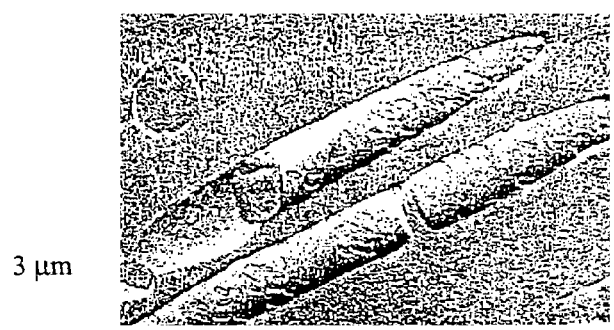
FIG. 3. is an image of *C. aurantiacus* by a scanning electron microscope.
Figure 4:
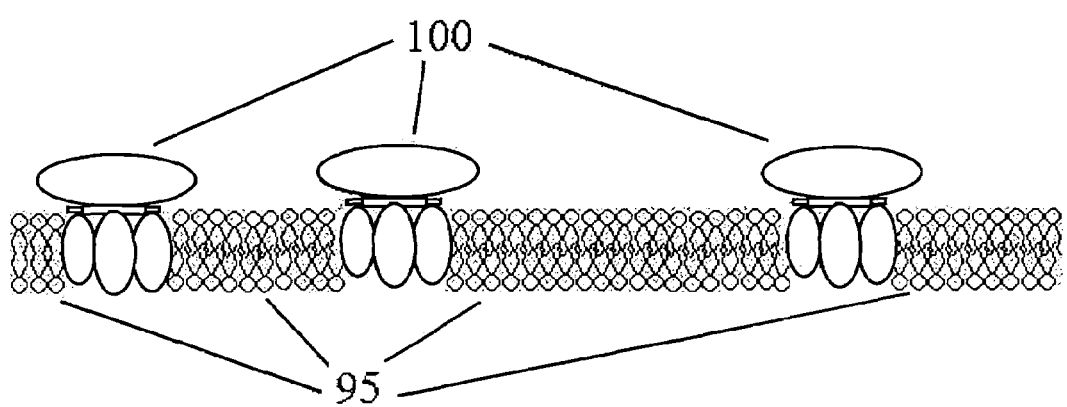
FIG. 4 is a cartoon schematic rendering of chlorosomes of *C. aurantiacus* in place in a cytoplasmic membrane.

A freeze fracture image of *C. aurantiacus* by scanning electron microscopy (SEM) was taken and is reproduced in FIG. 3. In the image small ovals can be resolved. These are the cell's chlorosomes. At this size scale reduction would require specialized EM or other imaging techniques. Thus far, no high resolution structural information has been successfully obtained on individual chlorosome structures, and as such a cartoon schematic representation of the chlorosomes 100 in situ is presented in FIG. 4. There, the chlorosomes 100 are depicted in place in a cytoplasmic membrane 95. A proposed model of a single chlorosome 100 is shown enlarged in FIG. 5 in a 3-D cartoon. From the work of Blankenship, et al., the chlorosome 100 is comprised of four major sub-units: a Bchl c portion 101, a Bchl baseplate 102, B808/866 protein, supra molecular light harvesting complex or apparati 103, and a reaction center (RC) 104.

Figure 5:
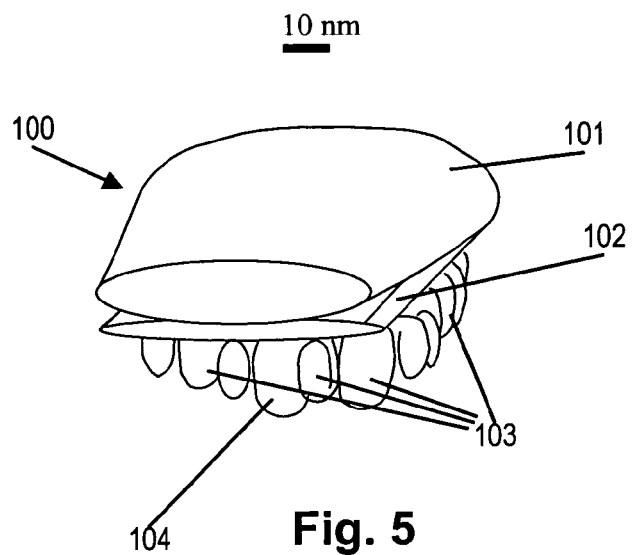
FIG. 5 is a diagrammatic (cartoon) illustration of a chlorosome of the bacterium *C. aurantiacus* with its four major subunits (the chlorosome designated herein the $RC^+$ chlorosome)
Figure 6:
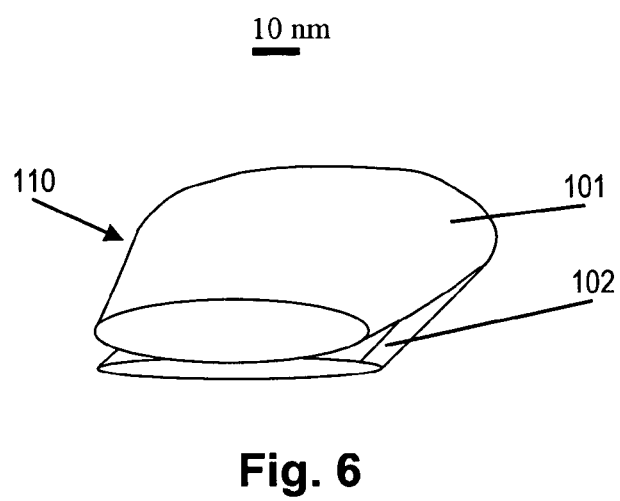
FIG. 6 is a diagrammatic (cartoon) illustration of the chlorosome of the bacterium *C. aurantiacus* of FIG. 5, but with two of its four subunits, the B808/866 protein light harvesting apparati and a reaction center removed (the chlorosome thus modified designated herein the $RC^-$ chlorosome)

A chlorosome 110 of the *C. aurantiacus* bacterium is depicted in FIG. 6. It includes two major supra-molecular pigment-protein subunits. These are the bacteriochlorophyll (Bchl) c 101, and the supra-molecular baseplate complex 102. In its form shown in FIG. 5 the *C. aurantiacus* chlorosome 100 is here designated RC+ (meaning with its RC 104 and B808/866 light harvesting apparati 103 in place). As depicted in FIG. 6 at 110, stripped of its associated reaction center and B808/866 supra-molecular complex 103, the chlorosome of *C. aurantiacus* is designated RC− (meaning without the RC 104 and B808/866 light harvesting apparati 103). Each sub-unit of the chlorosome 100 illustrated in FIG. 5 is composed of a large number of wavelength-specific light absorbing and transducing molecules.

Figure 7:
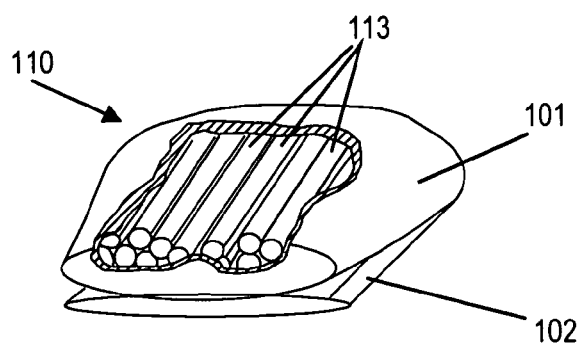
FIG. 7 is a diagrammatic (cartoon) illustration of the chlorosome of FIG. 6 with parts broken away for clarity showing contained rod-like structures of Bchl c.
Figure 8:
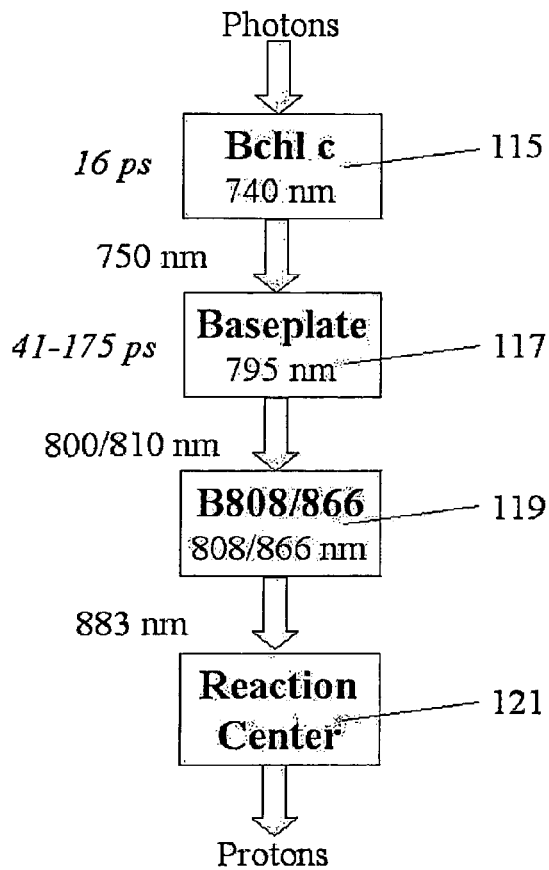
FIG. 8 is a functional block diagram in the form of a flow chart of optical interactions of the components of the chlorosome shown in FIG. 5.

The first sub-unit involved in light transduction is a lipid sack 101 containing bacteriochlorophyll (Bchl) c, which is organized in units of approximately 10,000 molecules that form rod-like structures 115 (FIG. 7). As represented in the flow chart of FIG. 8 at 115, these molecules transduce photonic energy associated with 740 to 750 nm light in approximately 16 ps with very little loss. Photonic energy at 750 nm is then transduced at 117 by the membrane of the baseplate 102, which is comprised of approximately 500 molecules of Bchl a, to 795 nm to 800/810 nm in 41–175 ps. The B808/866 complex 103 contains 10–20 Bchl a molecules, which absorb at 119 at 808 and 866 nm and transfer at 883 nm in approximately 250 ps. Finally, the last stage is where, at 121, a special pair of Bchl a molecules of the reaction center (RC) 104, convert the light energy into chemical (photochemistry) to emit photons.

Figure 9:
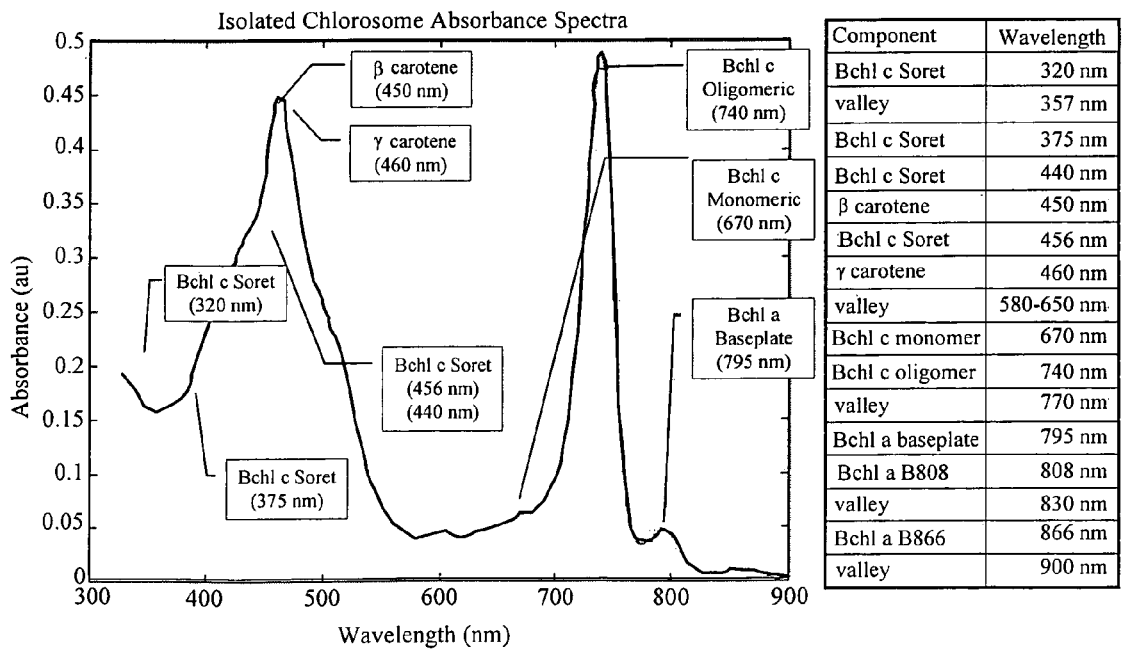
FIG. 9 is a plot of absorbent spectra data for a *C. aurantiacus* chlorosome.

FIG. 9 plots absorbance spectra data of isolated chlorosomes of *C. aurantiacus* noting peaks of interest. There, an absorbance peak at 740–750 nm attributable to the Bchl c rods 113 appears. A peak at 795 nm associated with the Bchl a baseplate is shown. In addition absorption of light in the blue region by the cartenoids is evident and blue secondary absorbance peaks from the Bchl c and a (designated as Soret peaks) occur. A peak attributable to the monomeric form of Bchl c (like its Soret) has a different absorbance wavelength peak than the oligomeric form that comprises the rods 113 in the chlorosomes. Like the Bchl a baseplate peak, the Bchl c oligomeric c peak is in the near infrared (NIR).

Figure 9A:
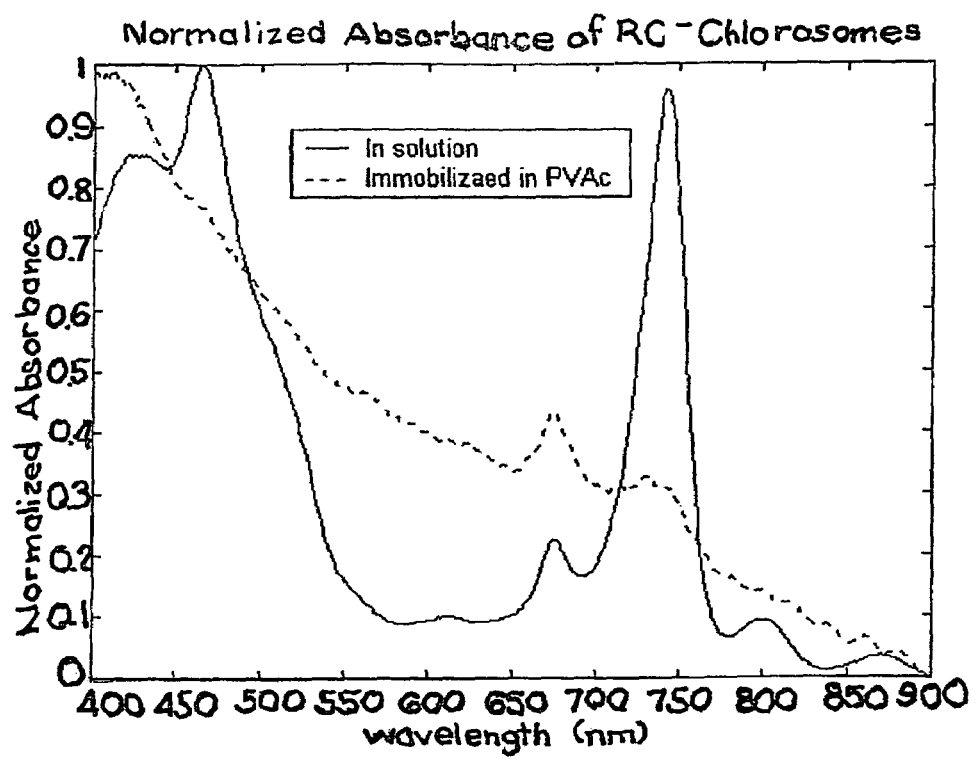
FIG. 9A is an exemplary normalized absorbance spectra plot of the $RC^-$ chlorosome.

Isolated RC− chlorosomes in Tris buffer exhibit the absorbance peaks (solid line) shown in the normalized absorbance spectral plot of FIG. 9A. Immobilizing the RC− chlorosomes in PVAC polymer, however, destroyed the chlorosomes as evidenced by the dashed line normalized absorbance spectrum plotted in FIG. 9A. This was true of other immobilization attempts with other polymers.

Figure 10:
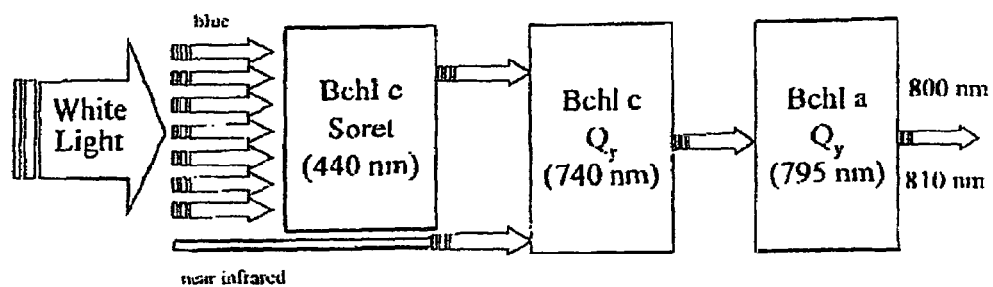
FIG. 10 is a diagrammatic block diagram in the form of a flow chart indicating the optical interaction of the parts of the chlorosome of FIG. 6.

Intact *C. aurantiacus* bacteria display a unique adaptive ability to reversibly and enzymatically assemble and disassemble the foregoing structures to protect the organism from photo-induced damage. As is expected, the spectral peaks of FIG. 9 are highly related to growth conditions of the whole cell *C. aurantiacus* bacteria. These are also related to the isolation techniques that result in purified chlorosomes. An abbreviated form of the important basic mechanisms of energy transfer that occur between the molecules of the RC− chlorosome are as depicted in FIG. 10.

The carotenoids have been shown to also transfer energy to the Bchl c oligomeric rods as is true of the Soret band (a strong absorbance of a chlorophyll in the blue region of light). However, there are subtle differences in the Bchl c found in the chlorosomes. The Bchl c found in *C. aurantiacus* chlorosomes are self-assembled (from monomeric form) into oligomeric rods. This results in a shift of the normal Soret (and $Q_y$) band into a redder form. The Bchl a found in the baseplate also has a Soret region in its photonic (blue) spectra. Carotenoids can begin to quench the structures and should be closely watched, as this would cause the device of this invention to operate at lower efficiencies.

Figure 11:
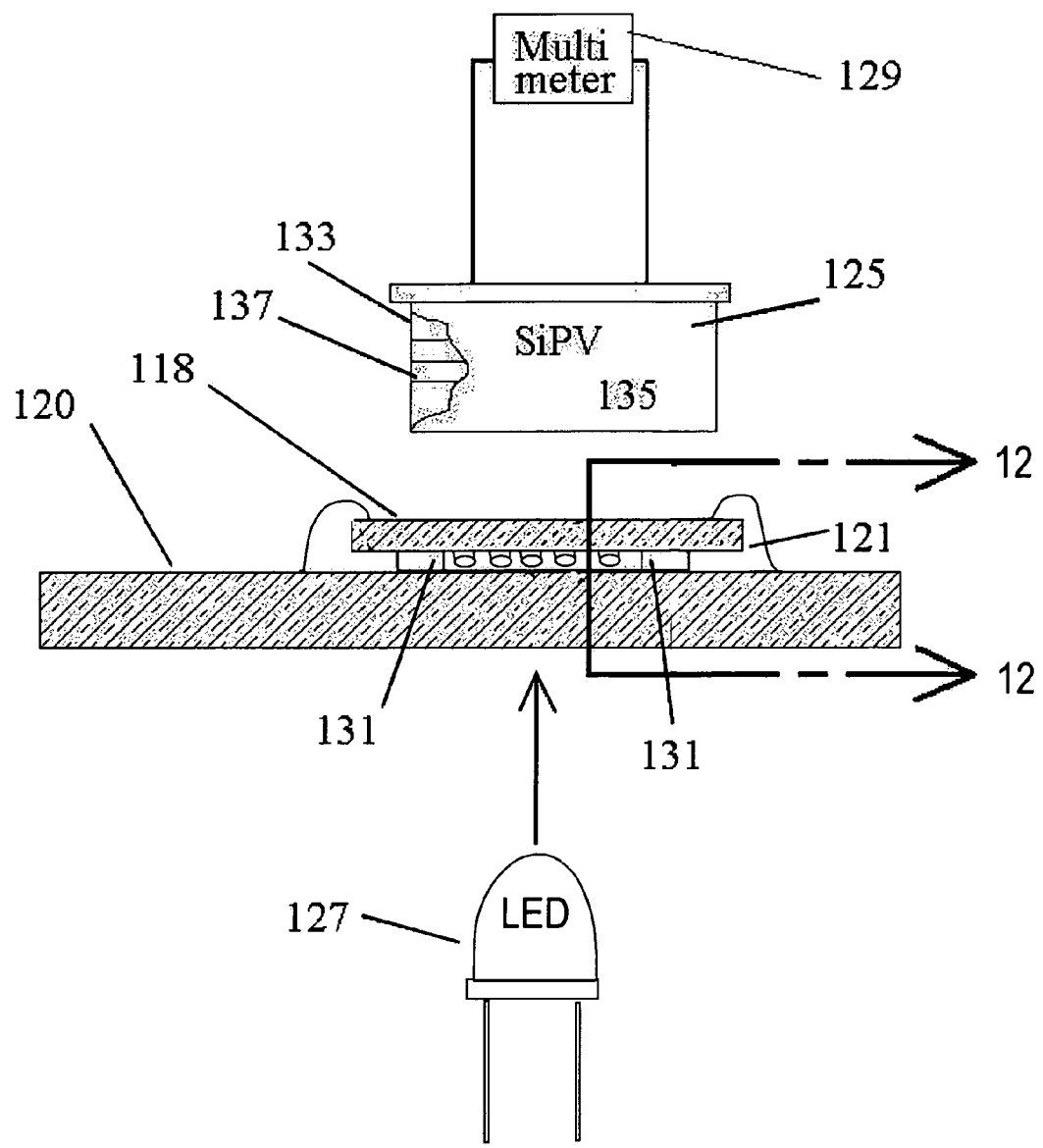
FIG. 11 is a diagrammatic illustration, partly in section, of a hybrid photovoltaic device in accordance with the invention.

In the exemplary embodiment of the invention that was successfully made and tested, the RC-chlorosomes were suspended in a liquid which was then applied to the hydrophobic surface of a borosilicate glass plate 118 as shown in FIGS. 11 and 12. It is the basis 102 of the chlorosomes 110 that adhere to the surface of the plate 118.

As shown in FIG. 11 the plate 118 is supported just above the surface of a glass slide or substrate 120. An epoxy seal 121 is formed about the edges of the plate 118. On or closely spaced above the plate 118 a commercially available silicon photovoltaic cell is supported. Illumination of the chlorosomes and the photovoltaic cell 125 by an LED 127 produces a voltage across the output of the photovoltaic cell 125 as can be observed by a multimeter 129.

Figure 18:
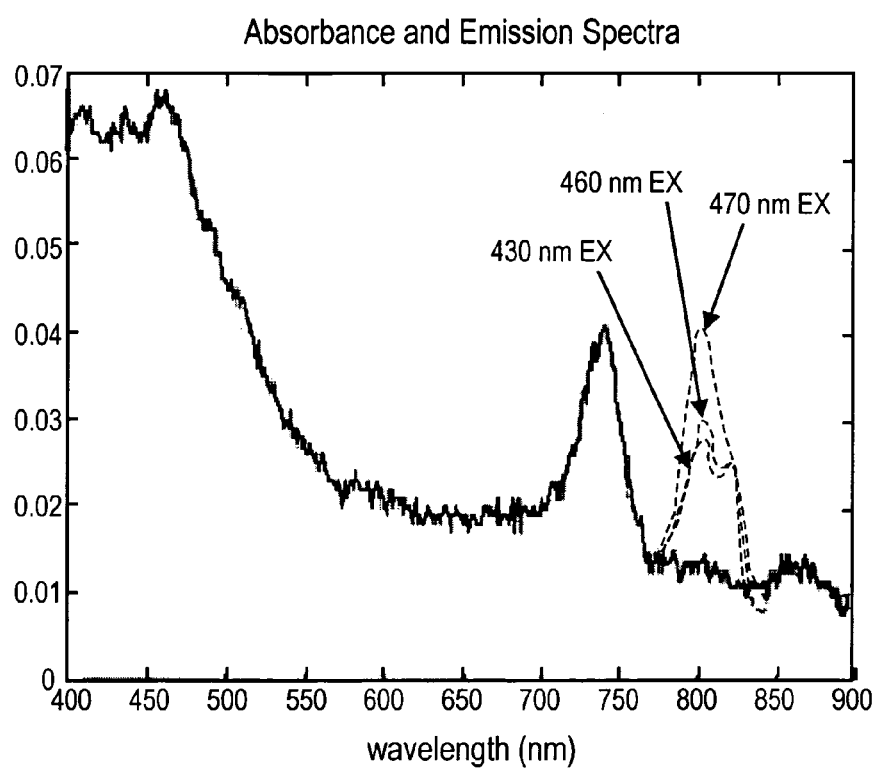
FIG. 18 is a plot of absorbance and emissions spectra of chlorosomes of *C. aurantiacus*.

As shown in FIG. 18, when excited with 430 nm, 460 nm and 470 nm, which is exactly where the silicon photovoltaic cells is less sensitive, the RC⁻ chlorosome emits at about 810 nm where the silicon photovoltaic cell is sensitive. There is, therefore, a spectral enhancement by the addition of the biological component that is similar to that shown generally in FIG. 18.

In an exemplary laboratory prototype of the device, the SiPV was an Edmond Optics NT53-371 photovoltaic cell. Slide 120 was a Fischer microwells slide, part number 12-568-20 and the plate 118 was a Fischer cover glass, part number 12-541A.

The microslide employed allowed for relatively straightforward application of the chlorosomes. This particular slide has two frosted rings on its surface, one of which is indicated at 131 in FIG. 11. The frosted ring was just sufficiently high above the surface of the slide 120 that a drop of the liquid suspension containing the chlorosomes was retained. The cover glass 118 was rested on the ring 131 and when the suspending liquid had evaporated leaving the chlorosomes adherent to the hydrophobic borosilicate cover glass surface as shown, the epoxy seal 121 was applied. The microwells slide was useful in another respect. Having two of the frosted rings 131, it permitted for the side-by-side construction as illustrated in FIG. 11 and a control. The control could be an identical silicon photovoltaic cell illuminated through the slide 120 and a further glass 118 but absent the chlorosomes, or the control could be as illustrated in FIG. 11 but having the RC⁺ chlorosomes entrapped.

In the arrangement of FIG. 11, the RC⁻ chlorosomes and the light receiving surface of the photovoltaic cells were no more than a millimeter apart. As indicated in FIG. 11, the construction of the off-the-shelf photovoltaic cell placed the light receiving surface 133 of the silicon semiconductor in a metal housing or can 135 to be exposed through a glass closure 137.

Characteristics of the biological component of the hybrid device of FIG. 11 are set forth in Table 1.

TABLE 1

Schematic Pictures of chlorosomes + Si PV

Chlorosome Characteristics

| | |
|---|---|
| Size: | 100 × 30 × 10 nm |
| Approx Rh: | 33 nm (calculated) 41 nm (DLS) |
| Energy Transfer: | |
| Strokes Shift: | 470–800/810 nm |
| Δλ: | 320 nm |
| QE: | 69–92% QE |
| Delay Time: | 50 ps–1 ns |
| Orientation | |
| Control: | Yes |
| Number of particles: | $4 \times 10^7$–$8 \times 10^9$ chlorosomes |
| Number of molecules: | $4 \times 10^{15}$–$8 10^{17}$ |

Experimental

Materials and Methods

First, the biological component (the RC chlorosomes), as well as controls, had to be isolated or purchased. Next, several types of characterization had to be performed (and developed in some cases) so that the device fabrication could be accomplished. These involved many steps (and iterations) until sufficient materials were readily available (in the correct form) for use in the hybrid device configuration.

*C. aurantiacus* cells were grown in 'D' media, under 6000 lux 50° C. in a one liter bottle (FIG. 3.2). The 'D' mixture is as follows (all chemicals from Sigma): A mixture of 50.0 ml of the medium D stock is added to distilled water with 2.0 gm Difco Yeast Extract, 1.0 gm Glycylgylcine (freebase) adjusting the pH to 8.2. This mixture is then autoclaved for 0.5 hr at 450° C. The medium D stock is prepared by mixing 40.0 ml of Nitch's Solution to 80.0 ml of the $FeCl_3$ solution in 3.51 of distilled water with the following traces: 8.0 gm Nitrilotriacetic acid, 4.8 gm of $CaSO_4.2H_2O$, 8.0 gm $MgSO_4.7H_2O$, 0.64 gm NaCl, 8.24 gm $KNO_3$, 55.12 gm $NaNO_3$, and 8.88 gm $Na_2HPO_4$. The Nitch's solution is made by placing 0.5 ml concentrated $H_2SO_4$, 2.28 gm $MnSO_4.H_2O$, 0.5 gm $ZnSO_4.7H_2O$, 0.50 gm $H_3BO_3$, 0.025 gm $CuSO_4. 7H_2O$, 0.025 gm $Na_2MoO_4. 2H_2O$, and 0.045 gm $CoCl_2. 6H_2O$ into 1 liter of distilled water. This should be stored refrigerated. The $FeCl_3$ solution is prepared by adding 0.2905 gm of $FeCl_3$ (or 0.4842 gm $FeCl_3. 6H_2O$) to 1 liter distilled water and should also be refrigerated.

RC⁻ chlorosome isolation (Gerola, 1986) starts with cells concentrated (600 ml) by centrifugation at 3,600×g for 60 min. 2M NaSCN with 10 mM ascorbic acid in 10 mM Pi buffer (6.5 ml monobasic: 43.5 ml dibasic phosphate buffer per liter) was added to the weighed pellet in 4 ml/gm amounts. Cells were homogenized 10× in a cell disruptor/homogenizer (Fisher Scientific). Disruption of cells was performed by (one) pass in a 4° C. stored French Press (ThermoSpectronic) cell with 20,000 psi. DNAse I (Sigma) was added and the solution was incubated for 30 min at room temperature. The solution was passed through the cell two more times.

Cell debris was removed by pelleting at 3,600×g for 1 hr. A continuous sucrose gradient was established by placing 2.0 ml of a 40% sucrose in the NaSCN buffer in a tube and layering on 3.0 ml of a 10% sucrose solution. The tubes were placed, horizontally, into a dark, 5° C. storage until use (48 hrs later). The addition of 1.2 ml chlorosome solution to the top and ultracentrifugation at 144,000×g for 18 hrs was started. Bands were collected by removal of the top band (by color), then removal by 1 ml at a time until the pellet was reached. The pellet was collected by addition of 1 ml to the tube and slight sonication to homogenize the pellet).

After isolation of the RC⁻ chlorosomes from *C. aurantiacus* whole cells, the chlorosomes were (at various dilutions into Tris buffer) tested as in the above methods. This was performed in order to assess quality control by comparing spectral data (on absorbance) and relative output (emission).

Surface effects (of the substrates) were tested by contact angle goniometry. This required a flat substrate (of sufficient surface area) to be placed on a Rame-Hart NRL Contact Angle Goniometer and test the contact angle with solution of known surface energies. Solution droplet formation was done with a syringe and about 100 µl droplet. Images were taken with the instruments CCD and using the RHI Imaging 2001 software to capture the digital pictures. Analysis can be done with the software. As well, as images were printed out and results were manually verified.

Another technique utilized the evaporation procedure as well as an aqueous method to allow incorporation of the chlorosomes onto a glass surface. Both techniques start with taking 0.5 µl of a known concentration of chlorosomes and placing it onto a borosilicate glass coverslip (Fisher Scientific). In the evaporation method, evaporation, under vacuum, is performed overnight and then the sample is sealed onto a fluorescent antibody microslide (Fisher Scientific). In the physical adsorption method, the slide is prepared in the aqueous phase and inverted during sealing, thus allowing for ensuring a hydrated sample as well as diffusion of the chlorosomes onto the surface of the hydrophobic glass. Samples were also studied under laser scanning confocal microscopy (instrument from LEICA) to investigate orientation and function (stability) was observed with absorbance spectroscopy of the sample afterwards.

The engineering photonic devices had to be characterized. Using a modified NIST approach to calibrate the detectors, a system to develop sensitivity curves (to wavelength) was established. Each device was calibrated under similar conditions and intensities were varied to demonstrate intensity changes (if present) in the device. Finally, devices that were to be enhanced had to be selected. Known nonlinearities in traditional devices, such as the silicon PV's (or solar cells) were selected as optimal devices for enhancement.

These devices were stimulated by white light filtered with interference filters to provide wavelength control from blue to NIR. Intensity was adjusted and matched using a radiometer from International Light (IL-1700). Changing the intensity from 0.01 to 70 lux caused a dramatic shift in the blue region by use of NDF's on an optical table (Edmund Optical Division).

The counting and size information gathering was accomplished by several high-resolution microscopy techniques. Transmission Electron Microscopy (TEM) was performed by taking isolated chlorosomes and evaporating a 0.5 µl drop onto a bacitracin treated formvar coated grid (300 mesh). Negative stains of urinal acetate were used to enhance the images. Images were taken at the Life Science EM Facility at 25,000× magnification. Images were saved in jpeg format, inserted into MATLAB and data (size and counts) were taken. Calculations were then scaled to predict how many chlorosomes were in a 1 ml sample for each of three dilutions. Absorbance spectroscopy of these dilutions was also performed to correlate absorbance spectra to count for the given population using a Beckman DU-65 photospectrometer (technique mentioned later).

A final method was used to gather most of the counting data, namely, Field Emission Scanning Electron Microscopy (FESEM) at the Center for Solid State Electronics Research Center at Arizona State University on a Hitachi 4700 FESEM. Again, a hemocytometer technique was employed as an initial method that could be correlated to the others. Another technique used computer aided image processing to allow the chlorosomes surface to be assigned a '1' or 'white' pixel value and the background a '0' or 'black'. Accounting for surface area (number of pixels) per chlorosome, histograms were made and counts were calculated via computer. The final technique was a modified ASTM method in which the surface is transversed from left to right, and top to bottom, counting chlorosomes until 100 is reached. Then the number of pictures required to reach ~100 chlorosomes, the surface area of each picture, etc are accounted for and a final # chlorosomes/ml is calculated. Here, five concentrations (plus a distilled water control) were imaged using all three techniques and counts were correlated to ABS spectra as well to aid in future calculations or determinations. The stubs were prepared by evaporating 100 µl of the dilution onto a hydrophobic borosilicate glass disk, attaching the disk to a stub via tape and carbon coating the samples for a period of 10 minutes. The chlorosomes were diluted with Tris buffer at pH 8.0 and 10 mM NaCl, by addition of 0.788 gm Trizma HCl into 500 ml of DI water, under constant stirring. Meanwhile, add 0.605 gm of Trizma Base was added into 500 ml of DI water under constant stirring. Both solutions were mixed together and 0.9 gm NaCl was added while mixture was stirred thus making 1 liter of 10 mM Trizma buffer, pH 8.0 with 20 mM NaCl.

Another imaging technique, namely Atomic Force Microscopy (AFM) was performed by evaporating a 100 µl sample of chlorosomes (overnight in desiccant jar) onto a standard borosilicate coverglass. A Digital Instruments' Nanoscope III Multimode AFM was used in Tapping Mode (TMAFM) to image the chlorosomes at various dilutions. Again, the dilutions' absorbance spectra were taken prior to imaging. Prior to running the AFM experiments, a known liquid volume (400 µl) was taken from solution containing $RC^-$ chlorosomes in DI water previously characterized via absorbance spectra (ABS=0.01@740 nm) and was evaporated onto a clean, optically clear glass disk with known surface area (113.1 mm$^2$). The disks were made hydrophobic to enhance $RC^-$ attachment and orientation due to theoretical studies performed by using a molecular modeling algorithm (Chou, 1977) that suggested that the baseplate region attached to the reaction center may be hydrophobic in nature. Tapping mode AFM experiments were conducted utilizing a small scan head (D head) to scan 1 µm$^2$ surface areas on both the control disks (no $RC^-$ chlorosomes deposited) and test disks ($RC^-$ chlorosomes deposited).

Ranges of dilutions were made by serial dilution of the stock chlorosome sample. Each dilution was placed into a standard cuvette (using a blank of Tris buffer) and full (400–900 nm) absorbance readings were gathered (via an RS232C port) onto computer and analyzed and plotted in MATLAB. At this point, selection of a non-pigment wavelength (650 nm in the case of the chlorosomes) was made to use in correlating absorbance to the previous counts made on each dilution and then plotted. This wavelength was selected for its non-photosynthetic (non-optically active) properties and consistent nature between different growth conditions during the counting experiments. Hence, a calibration curve was made between counting and absorbance for a series of dilutions of chlorosomes.

The TEM images were placed into the Image Processing Toolbox for MATLAB for sizing measurements and calculations processing. The scalebar was measured (in the number of pixels across it to length) and then correlated to the size of the bar so a conversion could be made for length and width of chlorosomes. The command 'ginput' was used to grab the distal ends of the chlorosomes and utilizing the Pythagorean Theorem: $a^2+b^2=c^2$, measurements of length and width were made by selecting random chlorosomes and measuring 5 per image. 25 chlorosomes from each image were selected and measured to ensure statistical distributions could be made. Counts (per µm$^2$) at this point were also made and calculations were made to correlate to a count per ml of each dilution and then related to the corresponding absorbance spectra.

In the AFM and FESEM studied, the images were taken and saved in jpeg format for processing in MATLAB as was done in the TEM images. Size was verified but in these techniques, counting was the main objective. The same process of taking the counts in an area and re-calculating what the count per ml was performed on many dilutions to enable a more accurate count (and correlation to absorbance data).

The same samples were sent to Protein Solutions Inc. DLS was run on the samples. Later (after purchase of a DLS system) 20.0 µl of each sample was injected via a gas-tight syringe into the quartz cuvette and readings were taken at 2 Acq/sec. Data filtering was performed to minimize dust events but capture the quickly diffusing small particles. The Dynamics V6 software developed the autocorrelation curves and produced the polydisperse plots of $R_h$ versus % mass for each sample.

During the AFM studies, the hydrophobicity of the baseplate was studied by utilizing differently treated coverglass in LSC. Untreated coverglass remained very hydrophobic, with a critical surface tension around 12 dynes/cm, a surface tension of 32 dynes/cm, and a contact angle (for DI water) of 41°. A heat treatment (450° C. for 4 hours) allowed for the coverglass to pass through the glass-transition ($T_g$) temperature and delivers the surface into a hydrophilic state (surface tension close to 12 dynes/cm and a contact angle of <1° for DI water). The samples were placed onto the surfaces (in a laminar flow hood to reduce contamination) and evaporated under vacuum over night. Imaging was performed within 36 hours of evaporation so that the chlorosomes would not swell (degrade). Images were taken and stored as jpeg format files and processed in MATLAB as with the other imaging techniques. Unusual formations or interactions at the surface were also imaged in the pictures. Placement of the concentrations required to make certain percent coverages into the microwells were done with an incubation time necessary for physical adsorption. The time was a predicted time based upon diffusion coefficient of the chlorosomes (as measured by DLS) and the path length. The final, assembled coverglass and microwells were sealed with a two-part epoxy and allowed to cure overnight.

The first stability test for the isolated chlorosomes tested storage under two conditions. A 'fresh' sample was maintained for use in 7° C. freezer and a long-term (or later called 'frozen') sample was placed in liquid nitrogen ($LN_2$). Initial degradation was noted in the samples and can be clearly seen (at the monomeric 670 nm absorbance peak) in the absorbance spectra of the 'fresh' sample. Emission spectra were even gathered to see if a decrease in emission occurred.

In intensity related photodegradation, concentrations were matched between all samples (six different intensities were investigated) by absorbance readings. Therefore, a series of experiments were designed and run with chlorosomes, with and without reaction centers, in solution, to see this effect. Samples were diluted to 1:100 of the original stock into Tris buffer. 2 ml each were separated out for 6 different light conditions. Light intensity was varied by the use of filters, no filter, or no light such that % Transmissions were 0% T, 14% T, 36% T, 53% T, 68% T, and 100% T and measured (photometrically). The light source was a standard 100-watt white light bulb. Degradation was recorded at times when 5, 10, and 15% degradation was noted. Degradation was quantified by noting a percent decrease in the 740 nm absorbance. The samples were continuously illuminated and at specific time intervals, absorbance readings were taken. Degradation of the 740 Bchl c $Q_y$ band was measured by (1) peak height from start to finish and by (2) integration of the area under the $Q_y$ band. Times were marked when 5, 10, and 15% degradation of the peak were attained. A control sample (buffer) was also held under the same illumination and used as the blank in the photospectrometer.

Next, in intensity related to concentration photodegradation experiments, various concentrations of chlorosomes (in 2 ml) were degraded by a similar white light (at fixed intensity). From these sets of experiments minimum photostress terms were calculated to determine a 0% degradation intensity (and time). Again, the 740 nm peak height provided a measure (by absorbance spectra) of photodegradation over time.

Another mode of destruction of the photo-stability of the chlorosomes could be simple denaturation (by acidity) by the buffer. Therefore, buffers (with a varying pH) were made from pH 2.0 to 12.0 and 1 ml of each was added to 1 ml of a chlorosome stock solution. Absorbance spectra as well as $R_h$ were measured for each sample. The $R_h$ was measured by testing 20 µl of the sample in the DLS system.

Heat (or temperature) induced photodegradation or denaturation was also explored and tested. Starting at room temperature, a water bath holding a vial of chlorosomes was brought to near boiling over a period of hours. During the experiment, absorbance readings were taken at about every 5–10° C. and degradation was calculated as mentioned previously.

Another mode of destruction of the photo-stability was tested by increasing the concentration of the chlorosomes, in solution to see if concentration aggregation could be attained. This was accomplished by use of concentration filters and measured by $R_h$. 15 ml of sample was concentrated down to differing volumes and the filtrate (buffer) was removed leaving a more concentrated sample. Then 20 µl of sample was removed for DLS measurements after absorbance spectra were taken to ensure viable sample and perform chlorosome counting.

A final experiment to show another mode of destruction of photo-stability was the addition of a competitor (for absorbance of blue light). Carotenoid solutions from the isolation procedure were reintroduced into the chlorosome sample (by dilution) and emission measurements were taken. Side control experiments were performed by addition of buffer alone. Stimulation was made by the RF-1501 Shimadzu spectrofluorometer and emission was measured on a photodiode after passage through an 800 nm interference filter (so that scatter and excitation energies could be removed). This also allowed for ratios of the Bchl c to a, Soret, and carotenoid peak to be calculated and compared for potential enhancement calculations for the hybrid well experiments.

The initial step in manufacture of the hybrid wells is the chlorosomes (or controls) themselves. First the isolated solution of chlorosomes had to be measured in order to determine the actual number of chlorosomes (per ml) in the solution. For the controls, this was done by number of molecules based upon molecular weight (fluorescein) or counts supplied by manufacturers (unlabeled and labeled particles). Next, calculations (and dilutions) had to be made in order to develop a varying percent coverage. When all coverages (and dilutions) were made, the procedure was the same. Place 20 µl of sample onto a hydrophobic coverglass and incubate in the laminar flow hood, in the dark, for at least 10 minutes. This gives the chlorosomes (or controls) enough time to physically adsorb onto the borosilicate glass surface. Next, invert the coverglass and place on top of the microslide holder centered on the frosted ring (1 cm in diameter). Sealing is performed by use of a 2-part (optical grade) epoxy. The samples are then placed in a microslide holder and stored over night (at least 24 hours) in the dark at room temperature. Further storage should be done at 5° C. in the dark.

The biophotonic hybrid device had to then be assembled, using the various interfacing techniques to integrate the chlorosomes (and controls), in a controlled, patterned array with the silicon (Si) photovoltaic (PV) photocell. Once fabricated, the device parameters or specifications had to be tested. These include: maximum output, time-response (or rise time), spectral sensitivity, intensity sensitivity, temperature sensitivity, and device lifetime.

The device was fabricated by utilizing physical adsorption immobilization to interface chlorosomes (on a glass substrate/microslide with well) to the Si PV photocell. The components were interfaced (mechanically) by a self-built optical chamber made from acrylic sheet. The microslide port was milled into one piece, holes were drilled for the fiber optic bundle and the Si PV detector. Accessory ports/chambers were made to fit 25 mm filters such as additive (or subtractive) and NDF for wavelength and intensity control, respectively. The whole apparatus was black felted to reduce external light leakage. Power was supplied using a standard variable power supply (for the LED) and the Si PV was monitored utilizing a digital multimeter (DMM).

In this arrangement, device parameters such as maximum output, time-response (or rise time), spectral sensitivity, intensity sensitivity, temperature sensitivity, and device lifetime were tested. Maximum output was monitored by allowing the device sufficient time to go from 0 millivolts (mV) to maximum for that particular LED intensity. The difference was recorded and compared to when no sample is introduced. This ratio was defined as normalized relative output in the following sections. Response time is defined as the time that required going from 0 to 90% of the final value during a switching on stage.

This was performed by timing a device versus the standard Si PV detector (no device attached). Spectral sensitivity was performed by replacing the LED with various colored LED's that covered the visible spectrum as well as into the near infrared (NIR). Voltages were recorded, and normalized relative outputs were made on the final device. All devices were tested using 470 nm, 735 nm, 880 nm, and white LED's (full spectra). Intensity sensitivity was verified using the blue (470 nm) LED since this was the wavelength of choice for enhancement.

Stability was verified by absorbance spectroscopy (400–900 nm) and degradation was recorded. Temperature of operation was also investigated and degradation was also monitored so that an operational range of temperatures could be established. In these experiments, data was also obtained to establish device lifetimes under such 'operational' conditions. The lifetime was determined by seeing what conditions led to device degradation and the time required to reach that point.

The devices (ranging from low to high percent coverages) were tested under LED illumination and ratios were made to the same detector under the same illumination (minus the hybrid wells) and percentages have been calculated. This percent enhancement signifies when a hybrid well device increases the measured output (and by how much percent) over the stand-alone configuration. The rise time (the time it takes to get from 10% to 90% final voltage) was measured and compared between the hybrid well devices to the stand-alone detector. This was accomplished with a stopwatch and DMM. White light LED (visible light) stimulation of a series of percent coverages have been conducted and compared to monochromatic results. White LED's were implemented into the device apparatus and run at a few intensities and on Si PV as well as Si TP. Device enhancement was not further enhanced by the addition of the full spectra light, in fact, red band quenching might have been recorded as noted by others (Klar, 2000) in other systems and setups. Using monochromatic light as the stimulation source intensities were run at different levels sufficient for device detection but lower than saturation (of device or hybrid component). Again, full range of percent coverages were evaluated and replicates run. Again, the detector's response (without the hybrid layer) was used as a point of reference in determining percent enhancement.

Other tests included data gathered from solution effect studies only. Temperature effects were determined by the previous experiment in which the chlorosomes' photostability to temperature changes was determined. Being in a bulk system in a water bath controlled environment fitted the design parameters of the hybrid well experiments and throughout testing, no experiments were conducted outside the 25–100° C. range. A series of hybrid devices were constructed and tested (positively) over a large period of time (and intensities). Further experimentation was conducted on these samples throughout the research endeavor until no (positive) responses were seen. Afterwards, the absorbance spectra of a few high percent coverages were measured using a home-built slide holder in the DU-65 Beckman Photospectrometer in order to check the status (photostability) of the chlorosomes.

Forced Adaptation

Inconsistent results initially plagued experiments leading to the development of the hybrid device of the invention. As noted, *C. aurantiacus* is self-adapting. This meant that chlorosomes taken from the same growth of cells could not be relied upon to behave consistently.

To overcome this lack of consistency force-adapted *C. aurantiacus* was developed having the performance desired. To this end, and because of the number of environmental variables involved in the growth of the cells and their substituent chlorosomes, a design of experiment (DoE) technique was employed to arrive at chlorosomes that performed well and consistently.

In relation to biophotonic device design, there are many pertinent issues in each stage of the design. Variables encountered throughout the entire process of making the hybrid photovoltaic device that are capable of affecting results are set out in Table 2. The design of the product stage (as tested by validation techniques) requires that the device be tested via an appropriate light source type and wavelength (such as a 470 nm LED) or a incandescent light bulb with correct interference filter (470 nm), and can be projected to the surface of the device with or without the aid of light pipes such as waveguides and/or fiber optics. The intensity that the device is stimulated with must also be of appropriate intensity as controlled by the voltage applied to the source (LED for example), a neutral density filter (NDF), or other means. Stimulation time must also be accounted for since the time of stimulation and intensity will correlate to a certain photostress that the device can handle before irreversible damage is done to the biohybrid layer. A controlled environment (for validation purposes) is also necessary (a dark room or constant intensity area), as well as selection of an appropriate measuring device, such as a high impedance digital multimeter (DMM) for photovoltaic devices for example.

Before the device can be tested however, materials must be acquired/produced and synthesized. These stages involve: growth of the bacteria and alteration (if any) of the chlorosomes. In this example, synthesis is governed by production in that changes in the chlorosomes can be induced by the growth period factors. Some of these factors include: intensity of light source, light type and wavelength (incandescent, LED, fluorescent); media (pH, temperature, components or strength); number of days allowed for growth (before isolation or media exchange); bottle-fill volume; and temperature. Some of these factors directly influence important design characteristics such as Figure of Merit (FoM), chlorosome size, photostability, and indirectly quenchers, to list a few.

Processing of the chlorosome requires isolation of the chlorosomes from the whole cell walls. This is done using a procedure well documented in the literature although certain factors do arise in the process. There are different procedures used to isolate chlorosomes without the reaction centers (RC⁻) versus those with (RC⁺). The solvents, agents, and buffer types used in the procedure are also very important and factors such as (the type, molarity, ionic strength, pH, and strength) all come into play. These factors will affect the state of aggregation and purity (and successful use) of the isolated chlorosomes.

Manufacture of the chlorosome layer is the step whereby means of immobilization (namely physical adsorption) a monolayer (or percent thereof) is deposited onto the surface of a substrate (borosilicate glass). Important factors for successful devices include: the fabrication conditions (temperature, incubation time, Light ON/OFF, and in the laminar flow hood); sealing method; concentration, volume, and % coverage (and hence interparticle distances); droplet placement (on the coverslip or in the well); and coverslip hydrophobicity, which all relate to chlorosome orientation (facing Si PV or LED).

Again, product final assembly is addressed above. However, other issues pertaining to lifetime of device and/or other issues such as post fabrication storage include factors of temperature, light intensity (and quality—i.e. wavelength) and # days, to name but a few.

TABLE 2

WELL ISSUES

| Growth | Isolation | Sample Fab | Sample Run |
|---|---|---|---|
| Intensity | Procedure | Fab conditions | Light Source type |
| | | Temperature | LED |
| | | Incubation time | Light bulb |
| | | Light ON/OFF laminar hood | W/wout F.O. |
| Media | Buffer Type | Buffer Type | Light Intensity $V_{applied}$ |
| | Molarity | Molarity | NDF used |
| | Ionic Strength | Ionic Strength | Measure tech. |
| | pH | pH | Stim. Time |
| | Temperature | Temperature | |
| pH | Aggregated? | Sealing method | Light wavelength $V_{applied}$ LED |
| Light type | Type (RC±) | Post fab storage | Holder |
| Incandescent | | Temperature | Sample holder |
| LED | | Dark | LED + NDF |
| Fluorescent | | # days | SiPV + LPF |
| Days of growth | Purity | % coverage | Intensity control |
| Bottle Volume | | Volume | Detector |
| Temperature | | Droplet placed | DMM used |
| | | On coverslip | 9 V (new) |
| | | In Well | High Imped. |
| Wavelength | | Coverslip hydrophobicity | Orientation Facing SiPV Facing LED |
| | | Concentration | Red LPF used Voltage Applied NDF used Room lights ON/OFF Stimulation time |

Figure 22:
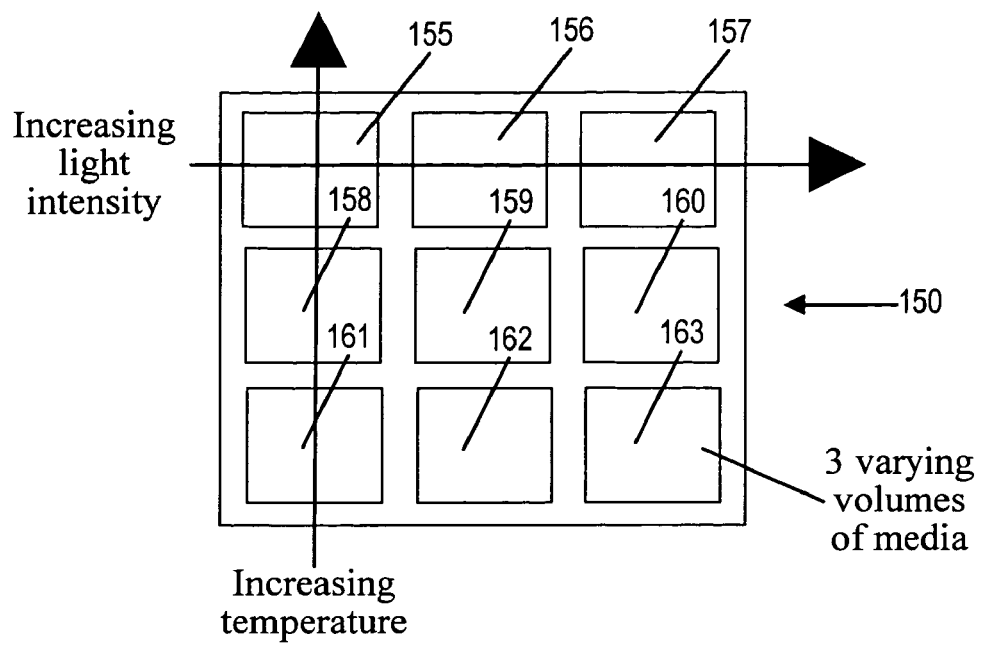
FIG. 22 is a diagrammatic illustration of a multiple input, multiple output environmental chamber having nine individual compartments.

In one stage of the development of the preferred exemplary procedures described in the above example, a multiple input, multiple output environmental chamber 150 (MIMO/EC) was constructed as diagrammed in FIG. 22.

Figure 23:
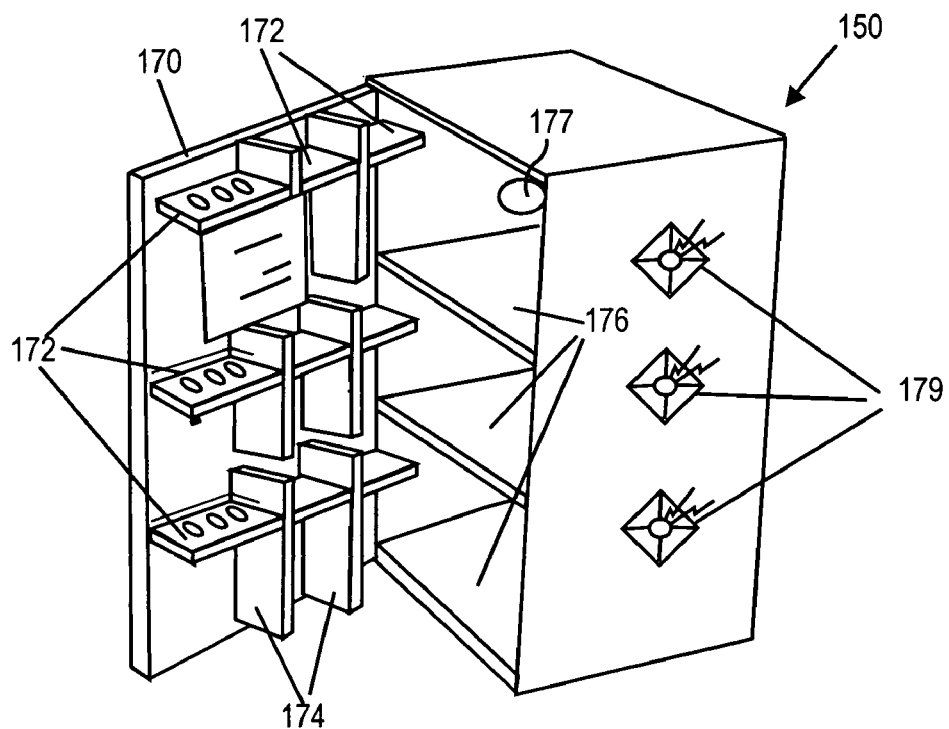
FIG. 23 a perspective view of an environmental chamber like that diagrammatically illustrated in FIG. 22

Nine compartments 155 through 163 were provided. Light intensity increased from left to right across the three columns of compartments and temperature increased from bottom to top across the three rows of compartments. Within the compartments three differing volumes of media were contained. Consequently, 27 combinations of variables were able to be tested. FIG. 23 illustrates an environmental chamber of this kind. On its door 170 multiple shelves 172 are supported and have openings to retain culture-containing rest tubes or containers. Vertical dividers 174 separate the compartments 155–163. Horizontal dividers 176 separate the compartments vertically. Light bulbs, one of which is shown at 177 provide illumination. A series of fans 179 regulate temperature.

Ordinarily in biology research is conducted on the OFAT, one factor at a time method. Here, the DOE approach permitted the three factors, light intensity, temperature and media to air volume ratio to be tested at three levels with three replicates and an additional three centerpoints and a total of 27 experiments ($2^3 \times 3 + 3 = 27$). The DOE technique allows for correlation of data statistically easier than OFAT or best-guess approaches. It reduces the total number of experiments, allows for a good, thought experimental design. It allows for error to be quantified and it can distinguish if factors have any to no effect or if interaction among factors occurs. Here, the response, the output under study, was concentration (by absorbent spectroscopy) after three days' growth.

EXAMPLE

A factorial design was chosen to quantify the relative importance of interaction between light intensity, temperature, and volume of media. The approach used was Design of Experiments (DOE). This method allows for data to be gathered in a way to avoid error by establishing an experiment protocol and quantify error in a mathematical way. The regression method that was used was the analysis of variance (ANOVA) technique. This tool (DOE) allows for data to be gathered at normal conditions (centerpoint) and at extremes (above and below the centerpoint). Analysis is based on quantifying effect and probability of effect of a factor or interaction on the output variable.

Cell Culture Stock

The cell culture stock was prepared for testing as in [1] and the MIMO/EC DOE culture incubation apparatus was also used. The data was gathered from nine strands that all came from a centerpoint grown stock (cultured at the centerpoint for 14 days). The data was gathered (randomly) at the end of a three-day growth cycle period and placed into the Stat-Ease™ software for analysis. Three replicates at each corner were taken as well as five centerpoint readings.

Pigment Protein Content Determination

The pigment protein content was deduced by taking absorbance spectra from 650 nm to 900 nm on each sample. This was done with a Beckman DU-65 photospectrometer. Then a ratio ($R_1$) was calculated by dividing the absorbance at 740 nm by that at 808 nm. Then another ratio ($R_2$) was calculated with the 740 over 866 nm peak absorbance readings. In this experiment, pigment protein content was desired to see an increase (larger chlorosomes).

Statistical Analysis Approach

The DOE approach used involves seven steps in order to perform the experiment. The first step involves defining the problem statement. Here it was desired to investigate which factors could increase the pigment protein content of the chlorosomes. Next, the choice of the factors, which may influence pigment protein content, had to be chosen. Also, the levels of these factors had to be established. The factors that were chosen, and their levels can be found in Table 3. below.

TABLE 3

Low, Centerpoint, and High Factor Levels for DOE Experiment

| Factor | Low (−) | Center | High (+) |
|---|---|---|---|
| A = Temp | 36° C. | 48° C. | 60° C. |
| B = Intensity | 50 lumen | 270 lumen | 490 lumen |
| C = Media | 5 ml | 7.5 ml | 10 ml |

The next step is to identify the output variable(s) to be studied. Since the change in pigment protein content was desired to be analyzed, the ratios of the 740 to 808 and 740 to 866 nm peak absorbances were chosen. The ratios were designated with a $R_1$ for the 740/808 and a $R_2$ for the 740/866 ratio. Since the choice of factors and levels were as stated, a $2^3$ factorial approach was chosen. In this approach, three replicates and five centerpoints were chosen also. The experiment was run at the end of a three day growth period and data was gathered in a random fashion. Since replicates were used the data analysis will not include determination normal % distribution plot and the analysis will really be based on the ANOVA tables. Interaction between factors was determined from the ANOVA as well as the interaction graphs provided by the software. Finally conclusions must be made based on the analysis and results.

The $R_1$ ratio developed strong effects due to each individual factor and the interaction between Temperature and % Volume. All other interactions were insignificant when compared to these four factors/interaction. This can be seen in the ANOVA table in Table 4. The normal % probability plot and interaction plot (between Temp and % Vol) can be found in FIGS. 11, 13a and 13b. Based on the analysis, the highest level for the $R_1$ ratio would be with bacteria grown under the following conditions: low temperature, low light intensity, and high % volume.

TABLE 4

ANOVA Table for experiment. Note DF represents degrees of freedom and CE is coefficient estimate. An appropriate prob>|t| was chosen to be 0.01 for this output variable therefore A, B, C, and AC have an effect on this output.

| Factor | CE | DF | Error | Prob>|t| |
|---|---|---|---|---|
| Intercept | 1.23 | 1 | $9.913 \times 10^{-3}$ | |
| A-Temperature | −.032 | 1 | $9.913 \times 10^{-3}$ | .0041 |
| B-Light Intensity | −.037 | 1 | $9.913 \times 10^{-3}$ | .0013 |
| C-% Volume | −.044 | 1 | $9.913 \times 10^{-3}$ | .0003 |
| AB | .027 | 1 | $9.913 \times 10^{-3}$ | .0118 |
| AC | −.056 | 1 | $9.913 \times 10^{-3}$ | <.0001 |
| BC | .015 | 1 | $9.913 \times 10^{-3}$ | .1372 |
| ABC | −.021 | 1 | $9.913 \times 10^{-3}$ | .0502 |
| Centerpoint | .41 | 1 | .024 | <.0001 |

Figure 14A:
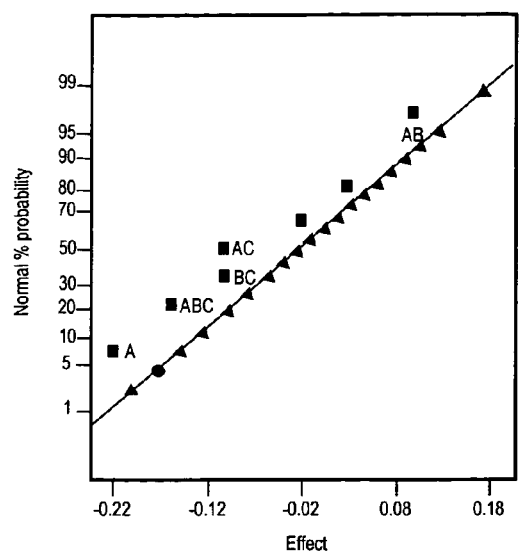
FIG. 14a is the normal percent probability plot and FIG. 14b the interaction plot between temperature and percent volume media to air for a design of experiments analysis where the output variable studied is the ratio R2 of absorbance at 740 nm to absorbance at 366 nm.
Figure 14B:
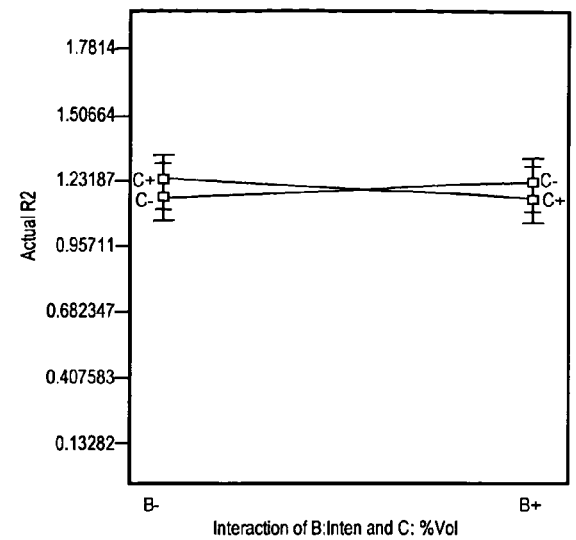

The $R_2$ ratio developed strong effects due to only temperature and no interactions. All other factors and interactions were insignificant when compared to temperature (see Table 5). The normal % probability plot and interaction plot (between Temp and % Vol) can be found in FIGS. 13a and 13b. As shown in FIG. 14a, the results are so close to the linear line that they are deemed insignificant except for temperature. Even the interaction plots (FIG. 14b) showed slight interactions. Note how the lines cross but the error bars overlap so that these lines could in fact be parallel and therefore non-interacting. The highest level possible for the $R_2$ ratio would be with bacteria grown under low temperature.

TABLE 5

ANOVA Table for experiment of $R_2$ ratio. Note DF represents degrees of freedom. An appropriate prob>|t| was chosen to be 0.1 for this output variable therefore A, B, C, and AC have an effect on this output.

| Factor | Coefficient Estimate | DF | Error | Prob<|t| |
|---|---|---|---|---|
| Intercept | 1.23 | 1 | .047 | |
| A-Temperature | −.11 | 1 | .047 | .0321 |
| B-Light Intensity | .032 | 1 | .047 | .5080 |
| C-% Volume | .006 | 1 | .047 | .8990 |
| AB | .049 | 1 | .047 | .3050 |
| AC | −.035 | 1 | .047 | .4651 |
| BC | −.036 | 1 | .047 | .4516 |
| ABC | −.077 | 1 | .047 | .1181 |
| Centerpoint | .51 | 1 | .11 | .0002 |

It is interesting to note from the results that the response variables (namely $R_1$ and $R_2$) are not dependent upon the same factors. $R_1$ is sensitive to temperature, light intensity, and % volume and the interaction of temperature and % volume. However, the $R_2$ ratio is dependent upon only the temperature during growth. This ratio was long believed to be only dependent upon light intensity but temperature was more significant. This may be due to the fact that the real dependent output is the $R_1$ ratio. If the bacteria are grown under those conditions and $R_1$ changes, $R_2$ must change as well but not vice-versa.

It is also possible that the temperature affects only the 866 nm molecules and light never changes growth (within limits selected in this study). Another, stronger argument is that since the natural funnel-like energy transfer in the chlorosome (from 740 to 795 to 808 to 866 nm molecules) protects the molecules further down the chain (like the 866 Bchl a) from being sensitive to factors such as light. At the same time, these molecules are still protein based and very dependent upon temperature effects.

TABLE 6

DOE experiment calculated data for pigment-protein growth/development ratios over a period of 6 transfers (3 weeks approximately).

| condition | ratio | Nov. 18, 1997 | Nov. 21, 1997 | Nov. 25, 1997 | Nov. 28, 1997 | Dec. 2, 1997 | Dec. 9, 1997 |
|---|---|---|---|---|---|---|---|
| − − − | 740/808 | 1.3182 | 1.2 | 1.1111 | 1.2174 | 1.25 | 1.0526 |
|  | 740/866 | 1.45 | 1.3333 | 1.1111 | 1.4 | 2 | 1.3333 |
| − − + | 740/808 | 1.2381 | 1.1071 | 1.16 | 1.28 | 1.2308 | 1.1667 |
|  | 740/866 | 1.3929 | 1.1273 | 1.2889 | 1.4545 | 1.4545 | 1.25 |
| − + − | 740/808 | 1.1579 | 1.0345 | .9231 | 1.1842 | 1.0526 | 1.017 |
|  | 740/866 | 1.2571 | 1.0526 | .8571 | 1.2857 | 1.0909 | 1.3 |

TABLE 6-continued

DOE experiment calculated data for pigment-protein growth/development ratios over a period of 6 transfers (3 weeks approximately).

| condition | ratio | Nov. 18, 1997 | Nov. 21, 1997 | Nov. 25, 1997 | Nov. 28, 1997 | Dec. 2, 1997 | Dec. 9, 1997 |
|---|---|---|---|---|---|---|---|
| −++ | 740/808 | 1.2353 | 1.375 | 1.2027 | 1.1667 | 1.2 | 1.4 |
|  | 740/866 | 1.377 | 1.5068 | 1.3692 | 1.3462 | 1.3548 | 1.4848 |
| +−− | 740/808 | 1.3333 | 1.2222 | 2.0732 | 2.1458 | 1.88 | 1.125 |
|  | 740/866 | 1.4545 | 1.375 | 2.2667 | 2.4235 | 2.0435 | 1.1538 |
| +−+ | 740/808 | 1.6 | 1 | 1 | 2.3368 | 1.7412 | 1.9759 |
|  | 740/866 | 2 | 1 | 1 | 2.6118 | 1.9221 | 2.2162 |
| ++− | 740/808 | 1.2857 | 1.0952 | 1.1579 | 1.2917 | 1.2687 | 1.25 |
|  | 740/866 | 1.4062 | 1.2778 | 1.2941 | 1.4531 | 1.4167 | 1.3514 |
| +++ | 740/808 | 1.1111 | 1 | 1 | 1.3049 | 1.2273 | 1.3929 |
|  | 740/866 | 1.3333 | 1 | 1 | 1.4079 | 1.35 | 1.56 |
| 000 | 740/808 | 1.7105 | 1.7901 | 1.7901 | 1.5854 | 1.686 | 1.5224 |
|  | 740/866 | 1.8571 | 1.9079 | 1.9595 | 1.6667 | 1.7262 | 1.619 |

Changes could clearly be seen from one transfer to the next. This suggests a forced evolution situation. The bacteria are being forced to survive in a hostile environment.

Take the +−− bacteria. In the first two transfers, it looked like it was dying and then by the third environment, some cells have adapted to the different environment and grown. Remember that the +−− was high temperature, low light intensity, and low amount of food source. Other changes can be seen in this sequence of pictures but clearly, this was the most significant.

The light intensity and the light-temperature interaction factors had coefficients of only one half the temperature factor in the 740 nm variable. This contrast was particularly apparent in those response variables that do not have photosynthetic activity. There is clearly a correlation between the light factor, the light and temperature interaction, and the absorbance of Bchl c (740 nm). Since the other response variables are mostly dependent on temperature, their changes can be primarily attributed to the change in absorbance which results from increased and/or decreased concentration of cells. Because cellular membrane components have an absorbance of 650–700 nm, the concentration of cells in each sample can be determined from the absorbance data in this region. By normalizing the data, it is possible to extrapolate the Bchl c absorbance for individual cells. This is the next logical step in analyzing the data.

Figure 15A:
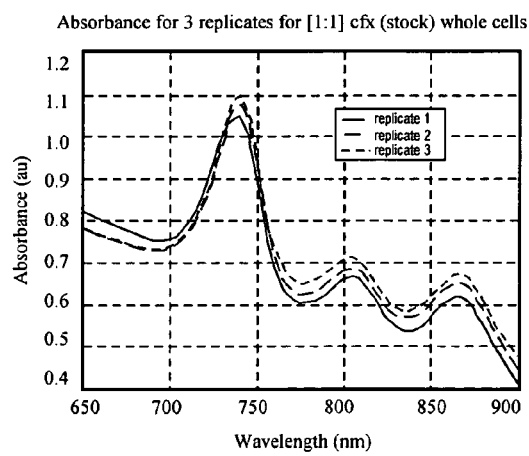
FIG. 15a is a plot of three replicates of a full spectra of *C. aurantiacus* at one dilution and FIG. 15b plots full spectra of absorbance of *C. aurantiacus* at multiple concentrations.
Figure 15B:
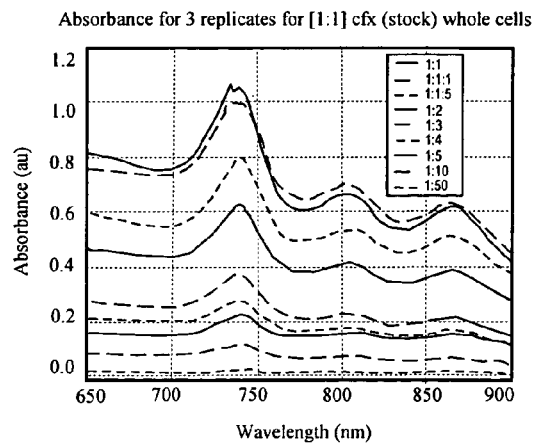
Figure 16A:
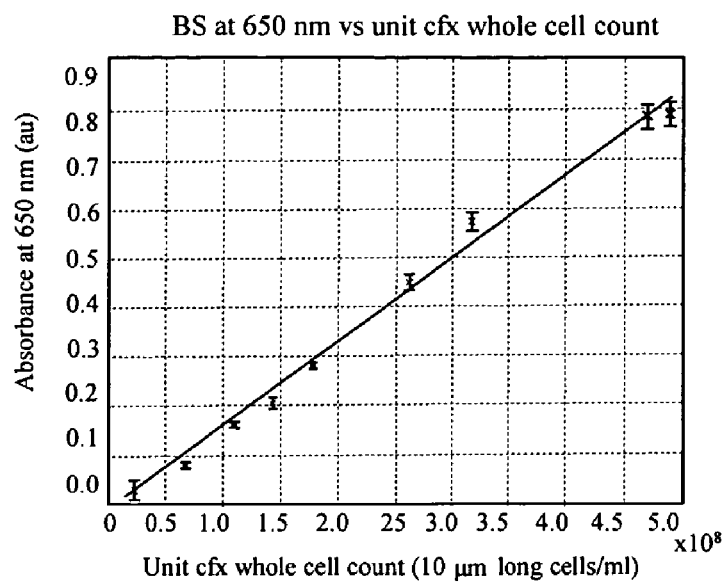
FIG. 16a is a plot of correlation between absorbance and cell count at 650 nm wavelength for *C. aurantiacus
Figure 16B:
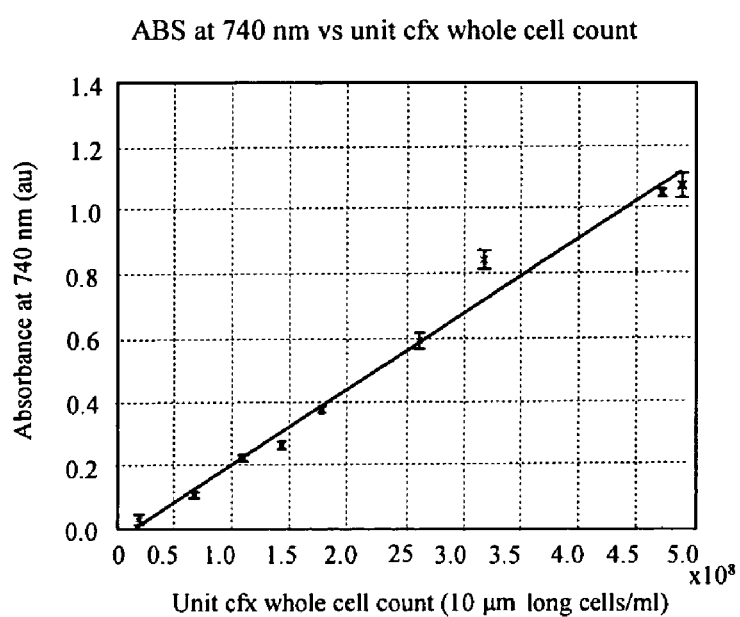
* and FIG. 16b is a plot of correlation between absorbance and cell count at 740 nm wavelength.

A method was developed to establish a faster process to count whole cells. A modified hemocytometry counting technique was used to count whole cell *C. aurantiacus* concentrations (per unit length of 10 μm), and absorbance data was gathered as three replicates of: 1:1, 1:1.1, 1:1.5, 1:2, 1:3, 1:4, 1:5, 1:10, and 1:50 dilutions were made. Full spectra (absorbance) data was gathered for each dilution, as in FIG. 15*a*. Each replicate was run to minimize instrument and operator error, FIG. 15*b* and peak data was gathered and averaged at 650, 740, 808, and 866 nm. The samples were then counted on an optical microscope using a standard red blood cell counting technique and a hemocytometer. In this fashion, curves were developed for absorbance at 650 and 740 mu and cellular counts with error bars as in FIGS. 16*a* and 16*b*.

Counting Chlorosomes

Figure 17:
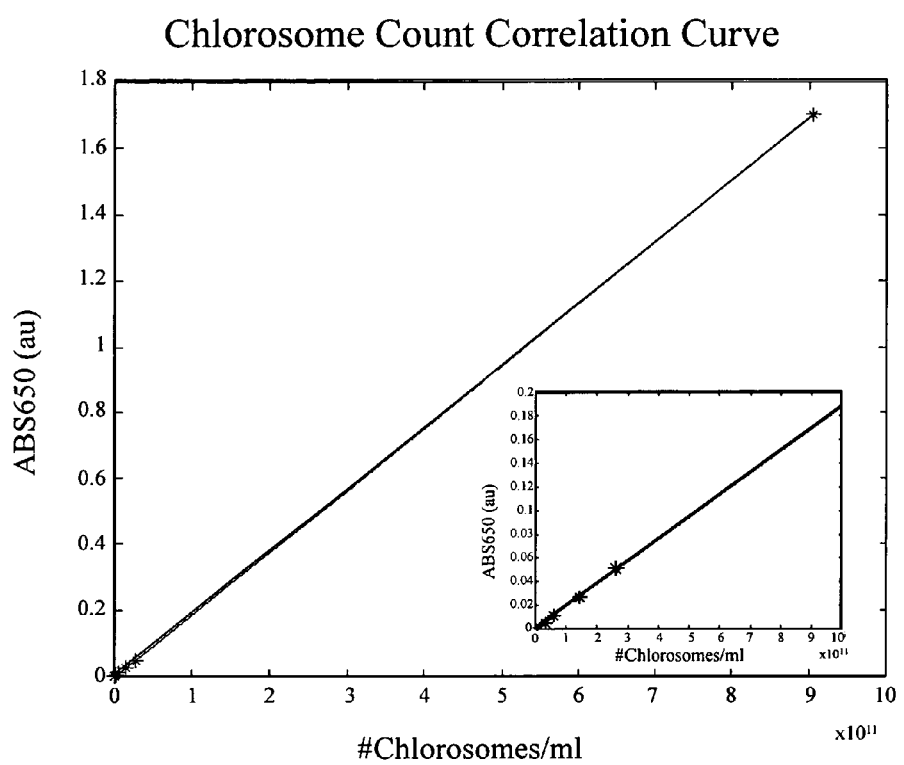
FIG. 17 is a plot of correlation between absorbance and number of $RC^-$ chlorosomes of *C. aurantiacus* at 650 nm wavelength and a zoomed-in-plot of the first four data points in that correlation showing close linearity between the two variables.

For the purposes of characterization and conformity in preparing the hybrid devices contemplated, determining the quantity of chlorosomes coating the cover glass hydrophobic surface was important. Absorbance of light was correlated to the density of chlorosomes as illustrated in FIG. 17. The calibration plot of FIG. 17 plots chlorosome count against chlorosome absorbance at the 650 nm wavelength. The 650 nm wavelength is chosen rather than a wavelength where absorbance of the chlorosome exhibits a peak because the absorbance at those wavelengths exhibiting a peak in the absorbance spectrum vary from one chlorosome to another depending, inter alia, on environmental factors effecting the growth of the bacterium from which the chlorosome was taken. The 650 m wavelength absorbance, then, is linearly related to chlorosome count and not another variable.

Figure 19:
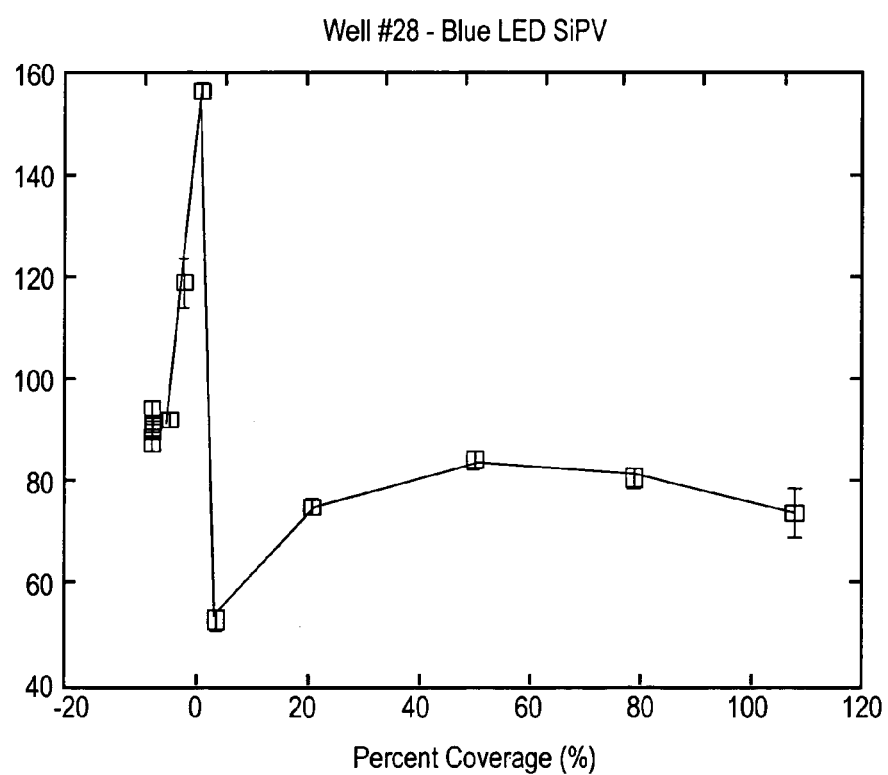
FIG. 19 is a plot of percent enhancement of a SiPV for percent coverage by chlorosomes of *C. aurantiacus;*
Figure 20:
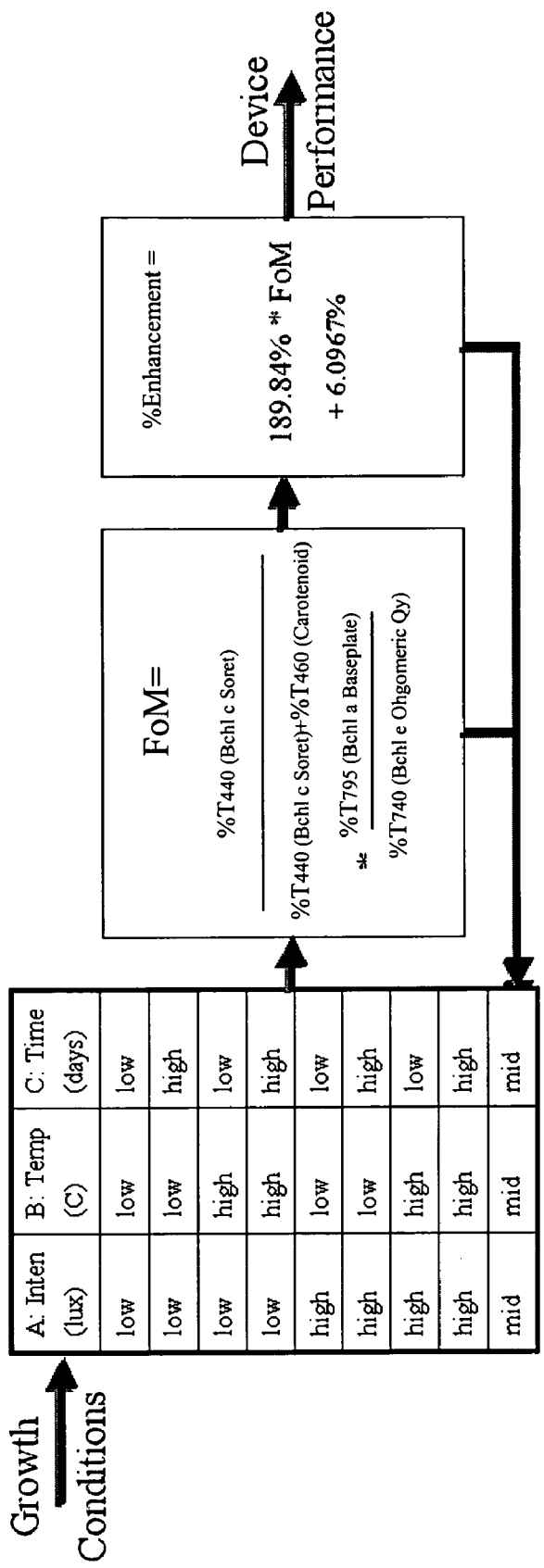
FIG. 20 is a functional block diagram that illustrates the use of a figure of merit in the development of a biological hybrid device with feedback from the Figure of Merit determination through a DOE or the like development program and feedback from the device performance.

In the exemplary preferred embodiment employing the chlorosomes of *C. aurantiacus* to enhance SiPV performance, chlorosome percent coverage of the SiPV's light receiving surface (or the overlying borosilicate glass) is important as demonstrated by the FIG. 19 plot of percent enhancement against percent coverage. Ideally, in this particular embodiment at least, coverage should be in the 4 to 7% range and preferably about 4%.

To arrive at percent coverage, accurate counting of the chlorosomes becomes important.

Figure 1:
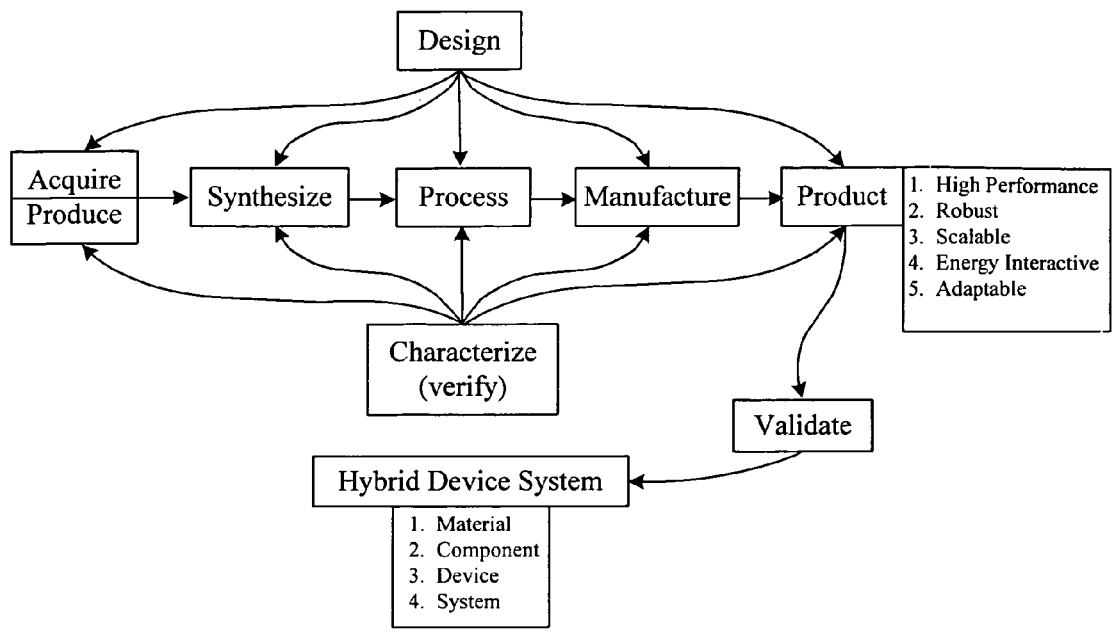
FIG. 1 is a conceptual block diagram illustrating elements in the design and development of a device, in particular a hybrid device of biological and nonbiological content.
Figure 2:
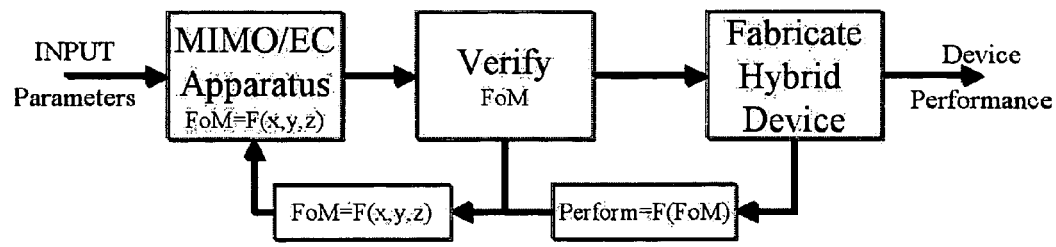
FIG. 2 is a conceptual flow chart of the design process for designing a hybrid device using a multiple input, multiple output environmental chamber and employing a figure of merit to gauge the performance of a biological component.

FIG. 1 is a conceptual block diagram that indicates the design and development of a hybrid device of the nature of the enhanced photovoltaic cell described above. At each stage of development multiple variables entered the design process. This is tabulated, as well, in Table 2. From this it will be seen that a robust program such as the design of experiments program that permits the assessment of multiple variables and their interaction is an enabling design tool in arriving at a final product that meets the objectives of high performance, robustness, scalability, energy interactivity and adaptability.

In the case of the enhanced hybrid photovoltaic device many pertinent issues arise at each stage of design. At the product stage, the device needs to be tested using an appropriate light source and wavelength, such as a 470 nm LED or an incandescent light bulb with a correct interference filter yielding 470 nm wavelength. Intensity is a variable. The use of suitable light waveguides or fiber optics may be a variable to consider. Stimulation time must be taken into account since it and intensity will correlate to a certain photostress that the device will be able to handle or not handle if irreversible damage is to be avoided. Controlled environments and appropriate measurement devices are to be chosen.

Before the device can be tested, however, materials must be acquired, and/or produced as by systhesization. Here the stages involve growth of the bacteria and alteration if that is needed to alter the chlorosomes that are to be employed. As has been seen, factors involved in the growth period can affect the chlorosomes, either beneficially or not. Some of these factors include light intensity, light type (i.e. incandescent, LED or fluorescent) and wavelength. Media (its PH, temperature, components, and strength) can affect chlorosome yielding bacteria development. The number of days allowed for bacterial growth (either before isolation of the bacteria or before an exchange of media) is another factor. Bottle-filled volume or, as has been shown, percent media to air and temperature are factors, as well. Some of these factors directly influence important design characteristics such as "Figure of Merit," discussed below, chlorosome size, chlorosome photostability, indirect quenching, etc.

Processing of the chlorosome requires isolation of the chlorosomes from the whole cells. As indicated above, this is done using procedures well documented. Nevertheless certain factors need to be taken into account during this process. These are the different procedures used to isolate chlorosomes without the reaction centers (i.e. the RC$^-$ chlorosomes vs. the RC$^+$ chlorosomes). Solvents, agents and buffer types used in the procedure are also important, and factors such as the type, molarity, ionic strength, pH and strength of these all come into play. These factors will affect the state of aggregation impurity of the isolated chlorosomes, and consequently the ultimate success of the design.

Manufacture of the chlorosomes layer is the step whereby means of immobilization (which is to say physical absorption) of a monolayer (or a percent of a monolayer) is deposited onto the surface of the substrate such as the borosilicate glass. Here, important factors for successful devices include the fabrication conditions of temperature, incubation time, lighting (on or off) and operation of a laminar flow hood. Sealing method, concentration volume and percentage of coverage enhance interpartical distances, dropment placement on the cover slip or in the well, and cover slip hydrophobisity all bear on chlorosome placement and orientation (i.e. either facing the SiPV or the LED in the preceding exemplary arrangements).

Final product assembly involves many of these same factors just raised, others described above and other factors commonly encountered in product production. Further concerns relate to device lifetime, postfabrication storage including temperature light intensity, type and wavelength are additional concerns.

From the above, then, it should be evident that best guess or one factor at a time approaches to design and development pale in comparison to the DOE approach.

Figure of Merit

"Figure of Merit" (FoM) is a concept employed widely and in many disciplines, although ordinarily not where biological matters arise. In the present invention a biophotonic Figure of Merit was devised to quantify chlorosome performance.

Figures 21A, 21B, 21C:
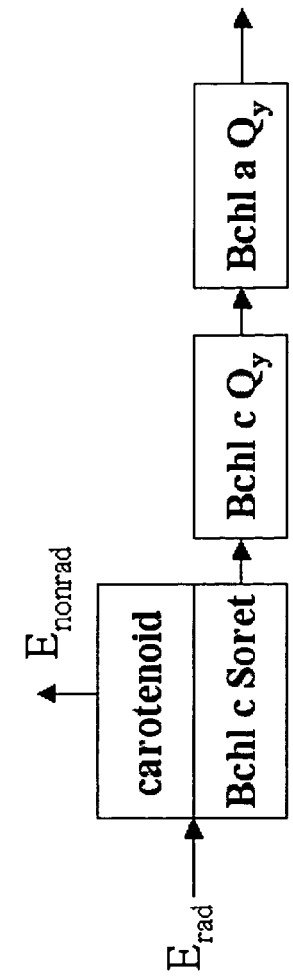
FIG. 21 is a formula for the photonic figure of merit devised for *C. aurantiacus,* a tabulation of the measures going into that formula for seven specimens and a block diagram illustrating the interaction of the major contributing factors to the figure of merit.

Bearing in mind the chlorosome functioning as conceptually diagrammed in the block diagram of FIG. 21a, the following Figure of Merit was devised.

$$FoM = \frac{\%T_{440(Bchl\ c\ Soret)}}{\%T_{440(Bchl\ c\ Soret)} + \%T_{460(Carotenoid)}} * \frac{\%T_{795(Bchl\ a\ Baseplate)}}{\%T_{740(Bchl\ c\ Oligomeric\ Qy)}}.$$

This FoM takes into account the total transmittance of the Bchl c Soret at 440 nm as compared to the total Soret and corrotenoid 460 nm transmittance and the baseplate Bchl a transmittance at 795 nm as compared to the Bchl c oligomeric transmission at 740 nm.

Engineering to a Figure of Merit in the exemplary embodiment of this invention was calculated to yield 160% of the Vout response of the original silicon photovoltaic cell at a Figure of Merit of 1.0. The actual improved output was measured at 157%.

Although preferred embodiments of the invention have been described in detail, it will be readily appreciated by those skilled in the art that further modifications, alterations and additions to the invention embodiments disclosed may be made without departure from the spirit and scope of the invention as set forth in the appended claims.

We claim:

1. A method of making a hybrid photoactive device, comprising:
    (a) providing photosynthetic chlorosome-containing bacteria *Chloroflexus aurantiacus*;
    (b) extracting the RC$^-$ chlorosomes from the bacteria;
    (c) providing a photoactive semiconductor; and
    (d) locating the RC$^-$ chlorosomes proximate a light receiving surface of the photoactive semiconductor, wherein step (c) includes providing a photoactive semiconductor having a light response that is diminished at a first range of light wavelengths, and step (a) comprises choosing an RC$^-$ chlorosome having
        (i) light response that is enhanced at a second range of light wavelengths that coincides, at least in part, with the first range of light wavelengths, and
        (ii) light emission outside the first range of light wavelengths, and wherein choosing an RC$^-$ chlorosome comprises force adapting bacteria with chlorosomes with the light response enhanced at the second range of light wavelengths and light emission outside the first range.

2. The method according to claim 1, wherein force adapting comprises
    (a) design of experiment determination of environmental factors forcing adaptation of bacteria based upon multiple environmental variables applied to *C. aurantiacus* sample bacteria; and
    (b) exposing the *C. aurantiacus* bacteria to an environment in which the factors identified in the previous step are present to force adapt the exposed *C. aurantiacus* bacteria.

3. The method according to claim 2, wherein force adapting comprises calculating a figure of merit for chlorosomes of the bacteria and identifying environmental factors resulting in an acceptable figure of merit.

4. The method according to claim 3, wherein the figure of merit is:

$$FoM = \frac{\%T_{440(Bchl\ c\ Soret)}}{\%T_{440(Bchl\ c\ Soret)} + \%T_{460(Carotenoid)}} * \frac{\%T_{795(Bchl\ a\ Baseplate)}}{\%T_{740(Bchl\ c\ Oligomeric\ Qy)}}.$$

5. The method according to claim 1, wherein the photoactive semiconductor diminished response is in the blue region of the visible spectrum and force adapting the bacteria comprises force adapting the bacteria to have chlorosomes responsive to light in said blue region to emit light outside said blue region.

6. The method according to claim 5, wherein the light emitted by the chlorosomes is light in the near infrared region of the visible spectrum.

7. A hybrid photoactive device made by the method of claim 1.

8. A hybrid photoactive device made by the method of claim 5.

9. A hybrid photoactive device made by the method of claim 6.

* * * * *